United States Patent
Hickey et al.

(10) Patent No.: US 11,998,692 B2
(45) Date of Patent: Jun. 4, 2024

(54) SECURE NETWORKED RESPIRATORY THERAPY SYSTEMS

(71) Applicant: ResMed Inc., San Diego, CA (US)

(72) Inventors: Brian Hickey, Dublin (IE); Christopher John Roberts, San Diego, CA (US); Chinmayee Somaiya, Sydney (AU); Wendall Eric Trull, San Diego, CA (US); Luke Anthony Tucker, Sydney (AU); Amila Jeewaka Fernando, Sydney (AU)

(73) Assignee: ResMed Inc., San Diego, CA (US)

( * ) Notice: Subject to any disclaimer, the term of this patent is extended or adjusted under 35 U.S.C. 154(b) by 0 days.

(21) Appl. No.: 18/162,343

(22) Filed: Jan. 31, 2023

(65) Prior Publication Data

US 2023/0248928 A1    Aug. 10, 2023

Related U.S. Application Data

(63) Continuation of application No. 16/347,359, filed as application No. PCT/US2017/059897 on Nov. 3, 2017, now Pat. No. 11,596,754.

(Continued)

(51) Int. Cl.
*G16H 20/40* (2018.01)
*A61M 16/00* (2006.01)
(Continued)

(52) U.S. Cl.
CPC ...... *A61M 16/024* (2017.08); *A61M 16/0066* (2013.01); *A61M 16/107* (2014.02);
(Continued)

(58) Field of Classification Search
CPC ............ A61M 16/024; A61M 16/0066; A61M 16/107; A61M 16/16; A61M 16/06;
(Continued)

(56) References Cited

U.S. PATENT DOCUMENTS

| 4,944,310 A | 7/1990 | Sullivan |
|---|---|---|
| 7,203,316 B1 | 4/2007 | Nolte |

(Continued)

FOREIGN PATENT DOCUMENTS

| CN | 102725015 A | 10/2012 |
|---|---|---|
| CN | 105122706 A | 12/2015 |

(Continued)

OTHER PUBLICATIONS

"Simple Pairing Whitepaper", Bluetooth Special Interest Group dated Aug. 3, 2006.

(Continued)

*Primary Examiner* — Tuyen K Vo
(74) *Attorney, Agent, or Firm* — Botos Churchill IP Law LLP

(57) ABSTRACT

Methods and apparatus provide communications among respiratory therapy device ("TD"), server and intermediary (e.g., a control device ("CTLD") for the therapy device) to improve security. More secure communication channel(s) may be established using shared secrets derived with different channels. The communications may include transmitting therapy data from TD to server for authentication. The CTLD may receive the data and a nonce from a server. The CTLD receives from the TD a signing key dependent on the nonce and a secret shared by TD and server. The CTLD generates an authorisation code with received therapy data and the key for authentication of the data by the server upon its receipt of the code and data. The server computes (1) a key from the nonce and the secret known to TD, and (2) another authorisation code from received therapy data and the key. Data authentication may involve comparing received and computed codes.

21 Claims, 13 Drawing Sheets

Related U.S. Application Data

(60) Provisional application No. 62/458,658, filed on Feb. 14, 2017, provisional application No. 62/416,867, filed on Nov. 3, 2016.

(51) Int. Cl.

| | | |
|---|---|---|
| *A61M 16/10* | (2006.01) | |
| *A61M 16/16* | (2006.01) | |
| *G16H 40/67* | (2018.01) | |
| *H04L 9/08* | (2006.01) | |
| *H04L 9/32* | (2006.01) | |
| *H04L 9/40* | (2022.01) | |
| *H04W 12/03* | (2021.01) | |
| *H04W 12/50* | (2021.01) | |
| *A61B 5/00* | (2006.01) | |
| *A61M 16/06* | (2006.01) | |
| *G06K 19/06* | (2006.01) | |

(52) U.S. Cl.
CPC ............ *A61M 16/16* (2013.01); *G16H 20/40* (2018.01); *G16H 40/67* (2018.01); *H04L 9/0841* (2013.01); *H04L 9/085* (2013.01); *H04L 9/0861* (2013.01); *H04L 9/3236* (2013.01); *H04L 63/061* (2013.01); *H04L 63/18* (2013.01); *H04W 12/03* (2021.01); *H04W 12/50* (2021.01); *A61B 5/4833* (2013.01); *A61M 2016/0027* (2013.01); *A61M 2016/003* (2013.01); *A61M 16/06* (2013.01); *A61M 16/109* (2014.02); *A61M 2205/3334* (2013.01); *A61M 2205/3553* (2013.01); *A61M 2205/3584* (2013.01); *A61M 2205/502* (2013.01); *A61M 2205/6009* (2013.01); *A61M 2205/6018* (2013.01); *A61M 2205/6072* (2013.01); *A61M 2209/01* (2013.01); *G06K 19/06028* (2013.01); *G06K 19/06037* (2013.01); *H04L 2209/80* (2013.01); *H04L 2209/88* (2013.01)

(58) Field of Classification Search
CPC ........ A61M 16/109; A61M 2016/0027; A61M 2016/003; A61M 2205/3334; A61M 2205/3553; A61M 2205/3584; A61M 2205/502; A61M 2205/6009; A61M 2205/6018; A61M 2205/6072; A61M 2209/01; A61M 16/022; A61M 16/0666; A61M 16/0069; A61M 2016/0039; A61M 2205/17; A61M 2205/3561; A61M 2205/3592; A61M 2205/52; A61M 2205/60; A61M 2205/7518; A61M 16/1055; G16H 20/40; G16H 40/67; G16H 10/60; H04L 9/0841; H04L 9/085; H04L 9/0861; H04L 9/3236; H04L 63/061; H04L 63/18; H04L 2209/80; H04L 2209/88; H04L 63/0435; H04L 63/123; H04W 12/03; H04W 12/50; H04W 12/04; H04W 12/106; A61B 5/4833; A61B 5/087; A61B 5/6814; A61B 5/0002; G06K 19/06028; G06K 19/06037; Y02A 90/10

See application file for complete search history.

(56) References Cited

U.S. PATENT DOCUMENTS

| | | |
|---|---|---|
| 7,778,422 B2 | 8/2010 | Freeman et al. |
| 7,866,944 B2 | 1/2011 | Kenyon et al. |
| 7,895,432 B2* | 2/2011 | Bjorn .................... H04L 9/321 713/168 |
| 7,955,258 B2 | 6/2011 | Goscha et al. |
| 8,636,479 B2 | 1/2014 | Kenyon et al. |
| 8,638,014 B2 | 1/2014 | Sears |
| 9,215,075 B1 | 12/2015 | Poltorak |
| 9,277,391 B2 | 3/2016 | Wan |
| 2002/0077856 A1* | 6/2002 | Pawlikowski ......... G16H 40/40 705/2 |
| 2005/0065572 A1 | 3/2005 | Hartley et al. |
| 2005/0109339 A1 | 5/2005 | Stahmann et al. |
| 2005/0145246 A1 | 7/2005 | Hartley et al. |
| 2011/0073107 A1 | 3/2011 | Rodman et al. |
| 2012/0124210 A1 | 5/2012 | Mass et al. |
| 2014/0133656 A1 | 5/2014 | Wurster et al. |
| 2014/0153724 A1 | 6/2014 | Kim |
| 2014/0281547 A1 | 9/2014 | Modzelewski et al. |
| 2015/0207796 A1 | 7/2015 | Love et al. |
| 2015/0248525 A1 | 9/2015 | Ury et al. |
| 2016/0242030 A1 | 8/2016 | Pang et al. |

FOREIGN PATENT DOCUMENTS

| | | |
|---|---|---|
| EP | 3051451 A1 | 8/2016 |
| FR | 2985829 A1 | 7/2013 |
| JP | 2004516562 A | 6/2004 |
| JP | 2013165518 A | 8/2013 |
| JP | 2014180062 A | 9/2014 |
| JP | 2016519458 A | 6/2016 |
| WO | 0249259 A2 | 6/2002 |
| WO | 2005091546 A2 | 9/2005 |
| WO | 2009075020 A1 | 6/2009 |
| WO | 2009119079 A1 | 10/2009 |
| WO | 2010141922 A1 | 12/2010 |
| WO | 2013020167 A1 | 2/2013 |
| WO | 2013076848 A1 | 5/2013 |
| WO | 2015179915 A1 | 12/2015 |
| WO | 2015179916 A1 | 12/2015 |
| WO | 2015179917 A1 | 12/2015 |

OTHER PUBLICATIONS

Chinese Second Office Action issued in corresponding CN application No. 2017800818873 dated Feb. 24, 2022.
Notice of Reasons for Refusal for Japanese Patent Application No. 2019-545705, dated Nov. 30, 2021.
Office Action for corresponding CN Application No. 2017800818873 dated Sep. 1, 2022 with English Translation.
PCT International Search Report issued in PCT application No. PCT/US17/59897 dated Jul. 5, 2018.
RFC 5054 (IETF memorandum), Nov. 2007.
Supplemental EP Search Report dated May 19, 2020 for EP Application No. 17897173.5.
The First Office Action for Chinese Patent Application No. 201780081887.3, dated Jun. 25, 2021.
Sayegh, Amir A., ""A Modified Secure Remote Password (SRP) Protocol for Key Initialization and Exchange in Bluetooth Systems"", First International Conference on Security and Privacy for Emerging Areas in Communications Networks (SECURECOMM' 05), pp. 261-269.
West, John B, "Respiratory Physiology", Lippincott Williams & Wilkins, 9th edition published 2011.
Notice of Allowance received in corresponding Japanese Patent Application No. 2019-545705, dated Mar. 10, 2023, 7 pages.
Office Action issued in corresponding Japanese Patent Application No. 2023-003985, mailed Apr. 26, 2024, 4 pages.

* cited by examiner

SECURE NETWORKED RESPIRATORY THERAPY SYSTEMS

1 CROSS-REFERENCE TO RELATED APPLICATIONS

This application is a continuation of U.S. patent application Ser. No. 16/347,359, filed on May 3, 2019, which is a national phase entry under 35 U.S.C. § 371 of International Application No. PCT/US2017/059897 filed Nov. 3, 2017, published in English, which claims priority from U.S. Provisional Patent Application No. 62/416,867, filed 3 Nov. 2016, and of U.S. Provisional Patent Application No. 62/458,658, filed 14 Feb. 2017, all of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use or operation.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *Respiratory Physiology*, by John B. West, Lippincott Williams & Wilkins, ninth edition, published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory failure (RF), Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by respiratory events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Respiratory failure is an umbrella term for respiratory disorders in which the lungs are unable to inspire sufficient oxygen or exhale sufficient CO2 to meet the patient's needs. Respiratory failure may encompass some or all of the following disorders.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of respiratory therapies have been used to treat such disorders.

2.2.2 Respiratory Therapies

Various forms of respiratory therapy, such as Continuous Positive Airway Pressure (CPAP) therapy, non-invasive ventilation (NIV) and invasive ventilation (IV) have been used to treat or ameliorate one or more of the above respiratory disorders. Furthermore, otherwise healthy individuals may take advantage of such therapies to prevent respiratory disorders from arising.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, MD and Chest Wall disorders.

Invasive ventilation (IV) provides ventilatory support to patients that are no longer able to effectively breathe themselves and may be provided using a tracheostomy tube.

High flow therapy is a respiratory therapy involving the application of a flow of air to an entrance to the airways at an elevated flow rate with respect to typical respiratory flow rate. HFT has been used to treat OSA and COPD.

Oxygen therapy is a respiratory therapy involving the application of a flow of oxygen-enriched air to an entrance to the airways at a prescribed flow rate. Oxygen therapy has been used to treat COPD.

2.2.3 Respiratory Therapy Systems

Respiratory therapy may be provided by a respiratory flow and/or pressure therapy system or device. A respiratory therapy system may comprise a respiratory therapy device (RT device) (e.g., a respiratory pressure therapy (RPT) device), an air circuit, a humidifier, a patient interface, an external control device, and a remote server.

2.2.3.1 Patient Interface

A patient interface may be used to interface a respiratory device to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as oxygen therapy, the patient interface, e.g. a nasal cannula, may not include a seal sufficient to facilitate delivery to the airways of a supply of gas at a positive pressure of about 10 $cmH_2O$.

2.2.3.2 Respiratory Therapy (RT) Device

An RT device may be used to deliver one or more of a number of therapies described above, such as by generating a flow of air at positive pressure for delivery to an entrance to the airways. Examples of RT devices include a CPAP device, a ventilator, and a portable oxygen concentrator.

2.2.3.3 Humidifier

Delivery of a flow of air without humidification may cause drying of airways. The use of a humidifier with an RT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 External Control Device

For reasons of cost and/or simplicity of manufacture, an RT device may have an extremely limited user interface comprising perhaps one or two buttons and LEDs, without a display screen. However, in such circumstances, the sophistication of the therapy deliverable via the RT device should be unimpaired. One way to accomplish both aims is for the RT device to be controllable by an external control device that is configured with the functionality to control the RT device to deliver respiratory therapy in all the variations of which the RT device is capable, such as by sending control parameters (e.g., pressure and/or flow rate settings). The external control device may take the form of a dedicated, pre-configured "remote control", or a general purpose computing device configured by running a special-purpose software application. For convenience, the external control device may be portable. In some such cases, the external control device may be configured to download the special-purpose software application(s), such as from a remote server over a network, e.g. the Internet, to achieve the functionality described in more detail herein.

Generally, such external control arrangements require the RT device to be in communication with the external control device. For convenience, particularly when the external control device is portable, the communication between the RT device and the external control device may be wireless. It is desirable to prevent security breaches of this arrangement by an unauthorised person also in possession of an external control device also configured to control the RT device. This is a particular challenge for wireless communication, which is in principle readily and surreptitiously accessible to unauthorised external control devices within range of the RT device. Protocols such as Bluetooth for short-range wireless communication between two devices may have a certain level of inbuilt security; however, they remain vulnerable to certain kinds of attack through unauthorised external control devices within range of the RT device as determined by the particular wireless protocol in use.

2.2.3.5 Remote Server

There may be clinical reasons to obtain data to determine whether the patient prescribed with respiratory therapy has been "compliant", e.g. that the patient has used their RT device according to one or more "compliance rules". One example of a compliance rule for CPAP therapy is that a patient, in order to be deemed compliant, is required to use the RT device for at least four hours a night for at least 21 of 30 consecutive days. In order to determine a patient's compliance, a provider of the RT device, such as a health care provider or device manufacturer, may operate a remote server that is configured to be in communication, such as periodically, with the RT device over a network. The remote server may obtain data describing the patient's therapy or results of an evaluation of one or more compliance rules from the RT device. The therapy data may be used to calculate the usage over a predetermined time period so as to be evaluated with the compliance rule(s) by the remote server and/or the RT device. Once a health care provider has determined that the patient has used their RT device in accordance with a compliance rule, the health care provider may notify a third party that the patient is compliant.

In addition, the "firmware" of the RT device may require upgrading from time to time. The RT device may obtain an upgrade file for such a purpose from a remote server operated by the device manufacturer via the network.

There may be other aspects of a patient's therapy that would benefit from communication between the patient's RT device and a remote server.

Securing such communications can be important for safety, compliance and/or privacy reasons. For example, ensuring that only proper upgrades are transmitted and applied to a receiving RT device can help to prevent tampering with the operations of the RT device. Similarly, ensuring that device-generated data is communicated without tampering can help to ensure the integrity of a compliance confirmation process. It can also be desirable to ensure that data transfer of health related information is limited to only intended or permitted recipients. Other benefits may be evident from the following description of several forms of the present technology.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

Aspects of the present technology relate to apparatus used in the diagnosis, amelioration, treatment or prevention of a respiratory disorder.

By means of some aspects of the present technology, a respiratory therapy device may be securely connected to a control device associated with an authorised user.

One form of the present technology comprises a method according to which a control device obtains, via physical access to a respiratory therapy (RT) device, a first shared secret, such as a token, known to the RT device. The first shared secret is then used by both devices communicating over an insecure communication channel to establish a relatively strong, more secure, second shared secret, such as a second more complex token, and thus establishing a secure communication channel between them. The secure communication uses the second shared secret in strong encryption methods.

Some versions of the present technology include a method of conducting wireless communications with a respiratory therapy device. The method may include establishing, by a control device, an insecure wireless communication channel with the respiratory therapy device. The method may include obtaining, by the control device, a first shared secret via a different channel than the insecure wireless communication channel. The first shared secret may be known to the respiratory therapy device. The method may include computing, by the control device, a second shared secret using the first shared secret and data communicated over the insecure wireless communication channel. The second shared secret may be known to the respiratory therapy device and being stronger than the first shared secret. The method may include conducting, by the control device, wireless communications with the respiratory therapy device based on the second shared secret.

In some versions of the method, computing the second shared secret may include a Diffie-Hellman key exchange. The method may include computing, by the control device, a session key using the second shared secret. The method may include using, by the control device, the session key to encrypt and decrypt data communicated with the respiratory therapy device over the wireless channel. In some versions, establishing an insecure wireless communication channel may include computing, by the control device, a symmetric key known to the respiratory therapy device. Obtaining the first shared secret via the different channel may rely on a physical access of the control device to the respiratory therapy device. Obtaining the first shared secret may include scanning, by the control device, a machine-readable form of the first shared secret printed on a housing of the respiratory therapy device. The machine-readable form may be a barcode. The barcode may be a QR code.

In some versions, obtaining the first shared secret comprises receiving, by the control device, the first shared secret entered via a user interface of the control device. The method may include confirming, by the control device, that the second shared secret is known to the respiratory therapy device. In some versions, the confirming may include computing a first hash value using the second shared secret; receiving from the respiratory therapy device over the insecure wireless communication channel, a second hash value; and comparing the first hash value with the second hash value. The method may include, upon the first hash value not being equal to the second hash value, generating user output via a user interface of the control device. The second shared secret may be used to establish a secure wireless communication channel between the control device and the respiratory therapy device. In some versions, the method may include computing a session key from the second shared secret. The method may include sending, by the control device over the secure wireless communication channel, a control parameter for controlling a respiratory therapy operation of the respiratory therapy device. The control parameter may include one of a pressure setting and a flow rate setting. The method may include receiving, by the control device over said secure wireless communication channel, data relating to respiratory therapy operation of the respiratory therapy device. The data may include any one or more of a number of respiratory events and a time of usage of the respiratory therapy device.

Some versions of the present technology may include a computer-readable data storage medium having program instructions encoded thereon configured to cause a processor to perform any of the method(s) described herein. Some versions of the present technology may include a server having access to such a computer-readable data storage medium. The server may be configured to receive requests for downloading the program instructions of the computer-readable data storage medium to the control device over a network. The server may send the program instructions in response to a request for downloading the program instructions.

Some versions of the present technology may include a control device configured to communicate wirelessly with a respiratory therapy device. The control device may include a memory storing processing instructions. The control device may include a processor. The processor may be configured to establish an insecure wireless communication channel with the respiratory therapy device. The processor may be configured to obtain a first shared secret via a different channel than the insecure wireless communication channel, the first shared secret being known to the respiratory therapy device. The processor may be configured to compute a second shared secret using the first shared secret and data communicated over the insecure wireless communication channel. The second shared secret may be known to the respiratory therapy device and may be stronger than the first shared secret.

In some versions, the control device may include a barcode reader. The processor may be further configured to obtain the first shared secret by utilising the barcode reader to scan a barcode printed on a housing of the respiratory therapy device. The barcode may encode the first shared secret. In some versions, the control device may include a user interface. The processor may be further configured to obtain the first shared secret via input entered through the user interface.

Some versions of the present technology may include a method of conducting wireless communications between a respiratory therapy device and a control device. The method may include establishing, by the respiratory therapy device, an insecure wireless communication channel with the control device. The method may include computing, by the respiratory therapy device, a second shared secret using a first shared secret and data communicated over the insecure wireless communication channel. The first shared secret and the second shared secret may be known to the control device. The second shared secret may be stronger than the first shared secret. The method may include conducting, by the respiratory therapy device, wireless communications with the control device based on the second shared secret.

Some versions of the present technology may include a respiratory therapy device configured to communicate wirelessly with a control device. The respiratory therapy device may include a memory storing processing instructions. The respiratory therapy device may include a controller configured to establish an insecure wireless communication channel with the control device. The controller may controller configured to compute a second shared secret using a first shared secret and data communicated over the insecure wireless communication channel. The first shared secret and the second shared secret may be known to the control device. The second shared secret being stronger than the first shared secret. The respiratory therapy device may include a housing including a printed barcode. The printed barcode may encode the first shared secret.

Some versions of the present technology may include a respiratory therapy system. The system may include a respiratory therapy device. The system may include a control device configured to communicate wirelessly with the respiratory therapy device. The control device may include a processor configured to establish an insecure wireless communication channel with the respiratory therapy device. The processor may be configured to obtain a first shared secret via a different channel than the insecure wireless communication channel. The first shared secret may be known to the respiratory therapy device. The processor may be configured to compute a second shared secret using the first shared secret and data communicated over the insecure wireless communication channel. The second shared secret may be known to the respiratory therapy device and may be stronger than the first shared secret. The processor may be configured to conduct wireless communications with the respiratory therapy device based on the second shared secret. The respiratory therapy device may include a housing with a printed barcode. The printed barcode may encode the first shared secret. The control device may further include a barcode reader. The processor may be further configured to obtain the first shared secret with the barcode reader by scanning the barcode. The control device may further include a user interface. The processor may be further configured to obtain the first shared secret via input entered through the user interface.

By means of other aspects of the present technology, therapy data uploaded from the respiratory therapy device to the remote server via an untrusted control device may be authenticated by the recipient.

Another form of the present technology comprises using a secret known to both the RT device and a server (but not the control device) and a "nonce" supplied by the server to derive (by the RT device) a key, which is used to derive an authentication code to authenticate the therapy data.

Some versions of the present technology may include a method of uploading therapy data generated by a respiratory therapy device to a remote server via a control device configured to communicate with the respiratory therapy device and to communicate with the remote server. The method may include receiving, by the control device, the therapy data from the respiratory therapy device. The method may include receiving, by the control device, a nonce from the remote server. The method may include sending, by the control device, the nonce to the respiratory therapy device. The method may include receiving, by the control device, a signing key from the respiratory therapy device. The signing key may be dependent on the nonce and a secret known to the respiratory therapy device and the remote server. The method may include generating, by the control device, an authorisation code using the therapy data and the signing key. The authorisation code may be for authenticating the therapy data. The method may include sending, by the control device, the therapy data and the authorisation code to the remote server. In some versions, the authorisation code may be a hashed message authorisation code. The signing key may be further dependent on an offset into the shared secret. The offset may be received from the remote server by the control device. The nonce may be a pseudo-random number. In some versions, the control device may receive the signing key securely from the respiratory therapy device by decrypting the signing key using a symmetric key that is known to the respiratory therapy device.

Some versions of the present technology may include a control device. The control device may include a memory, and a processor. The memory may contain program instructions that when, executed by the processor, control the control device to upload therapy data generated by a respiratory therapy device to a remote server. The program instructions may control the control device to receive the therapy data from the respiratory therapy device. The program instructions may control the control device to receive a nonce from the remote server. The program instructions may control the control device to send the nonce to the respiratory therapy device. The program instructions may control the control device to receive a signing key from the respiratory therapy device. The signing key may be dependent on the nonce and a secret known to the respiratory therapy device and the remote server. The program instructions may control the control device to generate an authorisation code using the therapy data and the signing key. The authorisation code may be for authenticating the therapy data. The program instructions may control the control device to send the therapy data and the authorisation code to the remote server.

Some versions of the present technology may include a method of authenticating therapy data generated by a respiratory therapy device. The method may include receiving the therapy data and a first authorisation code. The method may include computing a signing key from a nonce and a secret that is known to the respiratory therapy device. The method may include computing a second authorisation code from the received therapy data and the signing key. The method may include authenticating the therapy data by comparing the first authorisation code with the second authorisation code.

In some versions, the method may include sending an offset to the respiratory therapy device. The signing key may be dependent on the offset. The authorisation code may be a hashed message authorisation code. The method may include sending the nonce to the respiratory therapy device. The nonce may be a pseudo-random number.

Some versions of the present technology may include a server. The server may include a memory, and a processor. The memory may contain program instructions that, when executed by the processor, control the server to authenticate therapy data generated by a respiratory therapy device. The program instructions may control the server to receive the therapy data and a first authorisation code. The program instructions may compute a signing key from a nonce and a secret that is known to the respiratory therapy device. The program instructions may compute a second authorisation code from the received therapy data and the signing key. The program instructions may authenticate the therapy data by comparing the first authorisation code with the second authorisation code.

Some versions of the present technology may include a networked respiratory therapy system. The system may include a respiratory therapy device configured to deliver respiratory therapy to a patient. The system may include a remote server. The system may include a control device configured to communicate with the respiratory therapy device and to communicate with the remote server. The control device may be configured to receive, by the control device, therapy data from the respiratory therapy device. The control device may be configured to receive, by the control device, a nonce from the remote server. The control device may be configured to send, by the control device, the nonce to the respiratory therapy device. The control device may be configured to receive a signing key from the respiratory therapy device. The signing key may be dependent on the nonce and a secret known to the respiratory therapy device and the remote server. The control device may be configured to generate an authorisation code using the therapy data and the signing key. The authorisation code may be for authenticating the therapy data. The control device may be configured to send the therapy data and the authorisation code to the remote server. In some versions, the respiratory therapy device may be a respiratory pressure therapy device. The control device may be configured to communicate securely with the respiratory therapy device using a shared symmetric key. The remote server may be configured to receive the therapy data and a first authorisation code. The remote server may be configured to compute a signing key from a nonce and a secret that is known to the respiratory therapy device. The remote server may be configured to compute a second authorisation code from the received therapy data and the signing key. The remote server may be configured to authenticate the therapy data by comparing the first authorisation code with the second authorisation code.

Some versions of the present technology may include a networked respiratory therapy system. The networked respiratory therapy system may include a respiratory therapy device configured to deliver respiratory therapy to a patient. The networked respiratory therapy system may include a control device configured to communicate with the respiratory therapy device. The networked respiratory therapy system may include a remote server configured to communicate with the control device. The remote server may be configured to receive therapy data and a first authorisation code from the control device. The remote server may be configured to compute a signing key from a nonce and a secret that is known to the respiratory therapy device. The remote server may be configured to compute a second authorisation code from the received therapy data and the signing key. The remote server may be configured to authenticate the therapy data by comparing the first authorisation code with the second authorisation code. The respiratory therapy device may be a respiratory pressure therapy device. The control device may be configured to communicate securely with the respiratory therapy device using a shared symmetric key. The control device may be configured to receive the therapy data from the respiratory therapy device. The control device may be configured to receive a nonce from the remote server. The control device may be configured to send the nonce to the respiratory therapy device. The control device may be configured to receive a signing key from the respiratory therapy device. The signing key may be dependent on the nonce and a secret known to the respiratory therapy device and the remote server. The control device may be configured to generate an authorisation code using the therapy data and the signing key. The authorisation code may be for authenticating the therapy data. The control device may be configured to send the therapy data and the authorisation code to the remote server.

In some versions, the respiratory therapy device may be configured to receive a nonce from the remote server. The respiratory therapy device may be configured to compute a signing key from the nonce and a secret known to the respiratory therapy device and the remote server. The respiratory therapy device may be configured to generate an authorisation code using the therapy data and the signing key. The respiratory therapy device may be configured to send the therapy data and the authorisation code to the remote server.

Some versions of the present technology may include a method of uploading therapy data generated by a respiratory therapy device to a remote server. The method may include receiving, by the respiratory therapy device, a nonce from the remote server. The method may include computing, by the respiratory therapy device, a signing key from the nonce and a secret known to the remote server. The method may include generating, by the respiratory therapy device, an authorisation code using the therapy data and the signing key, the authorisation code for authenticating the therapy data. The method may include sending, by the respiratory therapy device, the therapy data and the authorisation code to the remote server. The authorisation code may be a hashed message authorisation code. The signing key may be further dependent on an offset into the shared secret. The offset may be received from the remote server by the respiratory therapy device. The nonce may be a pseudo-random number. The respiratory therapy device may receive the nonce via a control device configured to communicate with the remote server. The respiratory therapy device may receive the nonce from the control device by decrypting the nonce using a symmetric key that is known to the control device. The respiratory therapy device may send the therapy data and the authorisation code via a control device configured to communicate with the remote server. The control device may send the therapy data and the authorisation code to the control device by encrypting the therapy data and the authorisation code using a symmetric key that is known to the control device.

Some versions of the present technology may include a respiratory therapy device. The respiratory therapy device may include a pressure generator adapted to couple with a patient interface and to supply a flow of air at positive pressure to the patient interface. The respiratory therapy device may include a memory, and a processor. The memory may contain program instructions that, when executed by the processor, control the respiratory therapy device to upload therapy data generated by the respiratory therapy device to a remote server. The program instructions may control the respiratory therapy device to receive a nonce from the remote server. The program instructions may control the respiratory therapy device to compute a signing key from the nonce and a secret known to the remote server. The program instructions may control the respiratory therapy device to generate an authorisation code using the therapy data and the signing key. The authorisation code may be for authenticating the therapy data. The program instructions may control the respiratory therapy device to send the therapy data and the authorisation code to the remote server.

Some versions of the present technology may include a networked respiratory therapy system. The networked respiratory therapy system may include a respiratory therapy device for delivery of respiratory therapy to a patient. The networked respiratory therapy system may include a remote server configured to communicate with the respiratory therapy device. The respiratory therapy device may be configured to receive a nonce from the remote server. The respiratory therapy device may be configured to compute a signing key from the nonce and a secret known to the remote server. The respiratory therapy device may be configured to generate an authorisation code using therapy data and the signing key. The authorisation code may be for authenticating the therapy data. The respiratory therapy device may be configured to send the therapy data and the authorisation code to the remote server. The respiratory therapy device may be a respiratory pressure therapy device. In some versions, the networked respiratory therapy system may include a control device configured to communicate securely with the respiratory therapy device and to communicate with the remote server. The control device may be configured to communicate securely with the respiratory therapy device using a symmetric key that is known to the respiratory therapy device. The remote server may be configured to receive the therapy data and a first authorisation code. The remote server may be configured to compute a signing key from a nonce and a secret that is known to the respiratory therapy device. The remote server may be configured to compute a second authorisation code from the received therapy data and the signing key. The remote server may be configured to authenticate the therapy data by comparing the first authorisation code with the second authorisation code.

Some versions of the present technology may include an apparatus having means for receiving therapy data from a respiratory therapy device. The apparatus may include means for receiving a nonce from a remote server; means for sending the nonce to the respiratory therapy device. The apparatus may include means for receiving a signing key from the respiratory therapy device, wherein the signing key is dependent on the nonce and a secret known to the respiratory therapy device and the remote server. The apparatus may include means for generating an authorisation code using the therapy data and the signing key, the authorisation code for authenticating the therapy data. The apparatus may include means for sending the therapy data and the authorisation code to the remote server.

Some versions of the present technology may include an apparatus having apparatus means for receiving therapy data from a respiratory therapy device and a first authorisation code. The apparatus may include means for computing a signing key from a nonce and a secret that is known to the respiratory therapy device. The apparatus may include means for computing a second authorisation code from the received therapy data and the signing key. The apparatus may include means for authenticating the therapy data by comparing the first authorisation code with the second authorisation code.

Some versions of the present technology may include an apparatus having means for delivering respiratory therapy to a patient. The apparatus may include means for receiving a nonce from a remote server. The apparatus may include means for computing a signing key from the nonce and a secret known to the remote server. The apparatus may include means for generating an authorisation code using therapy data and the signing key, the authorisation code for authenticating the therapy data. The apparatus may include means for sending the therapy data and the authorisation code to the remote server.

The methods, systems, devices and apparatus described herein can provide improved functioning in a processor, such as of a processor of a specific purpose computer, respiratory monitor and/or a respiratory therapy device. Moreover, the described methods, systems, devices and apparatus can provide improvements in the technological field of automated management, monitoring and/or treatment of respiratory disorders, including, for example, obstructive sleep apnea, and in relation to communications with devices.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Therapy Systems

FIG. 1 shows a system including a patient 1000 wearing a patient interface 3000, in the form of nasal pillows, receiving a supply of air at positive pressure from an RT device 4000. Air from the RT device 4000 is humidified in a humidifier 5000, and passes along an air circuit 4170 to the patient 1000. A bed partner 1100 is also shown.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows a patient interface in the form of a nasal mask in accordance with one form of the present technology.

4.4 RT Device

4.5 Humidifier

Figure 5A:
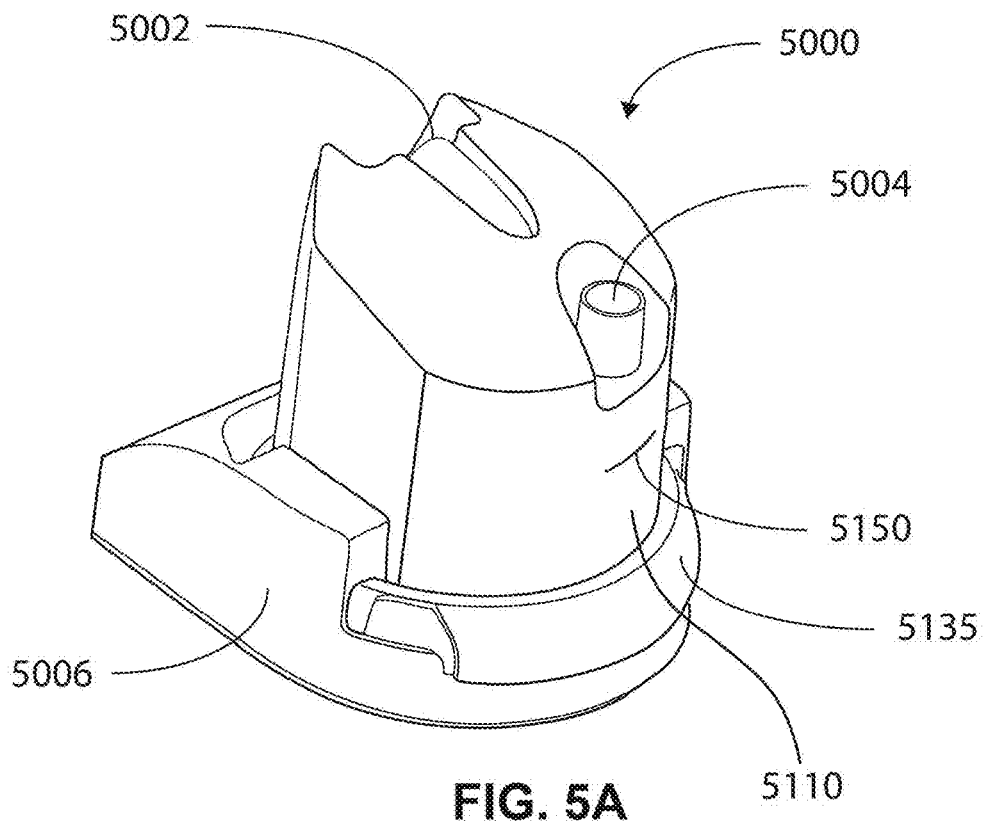

FIG. 5A shows an isometric view of a humidifier in accordance with one form of the present technology.

Figure 5B:
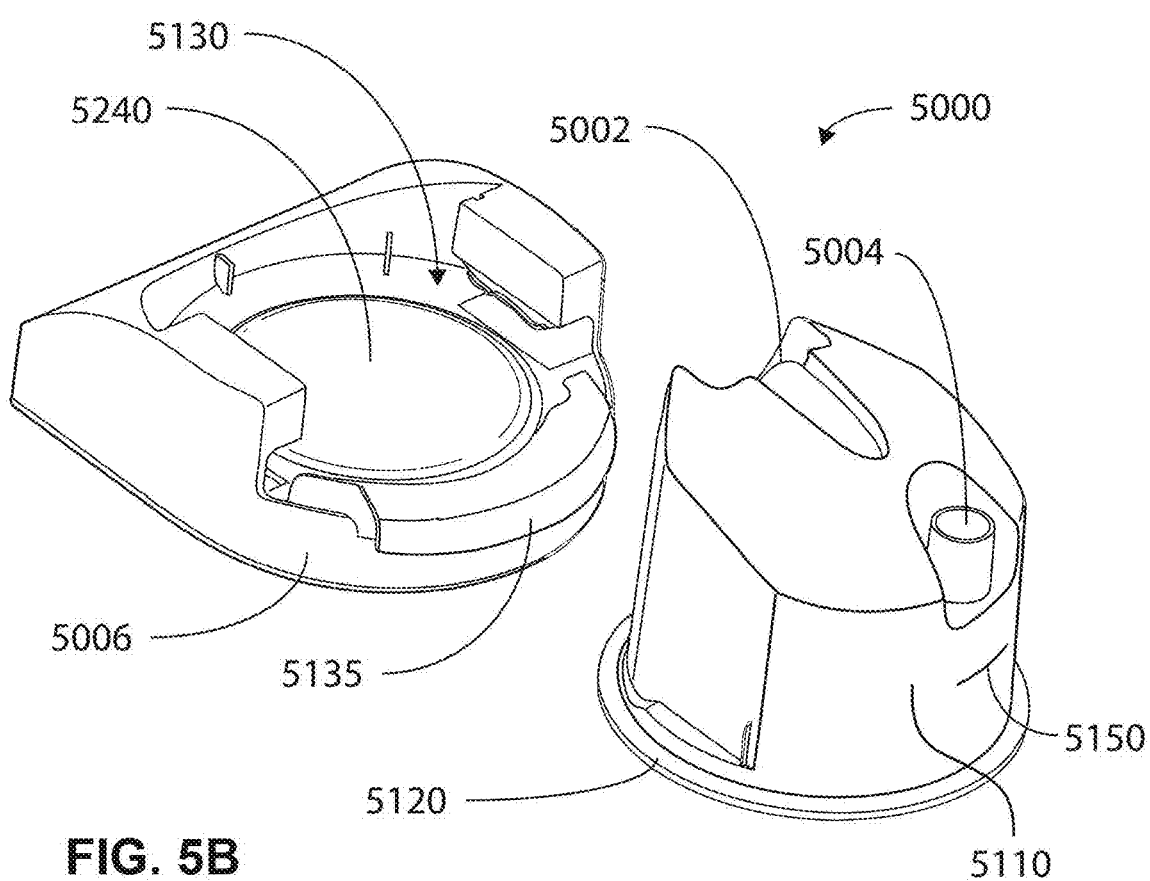

FIG. 5B shows an isometric view of a humidifier in accordance with one form of the present technology, showing a humidifier reservoir 5110 removed from the humidifier reservoir dock 5130.

4.6 Secure Networked Respiratory Therapy System

Figure 6:
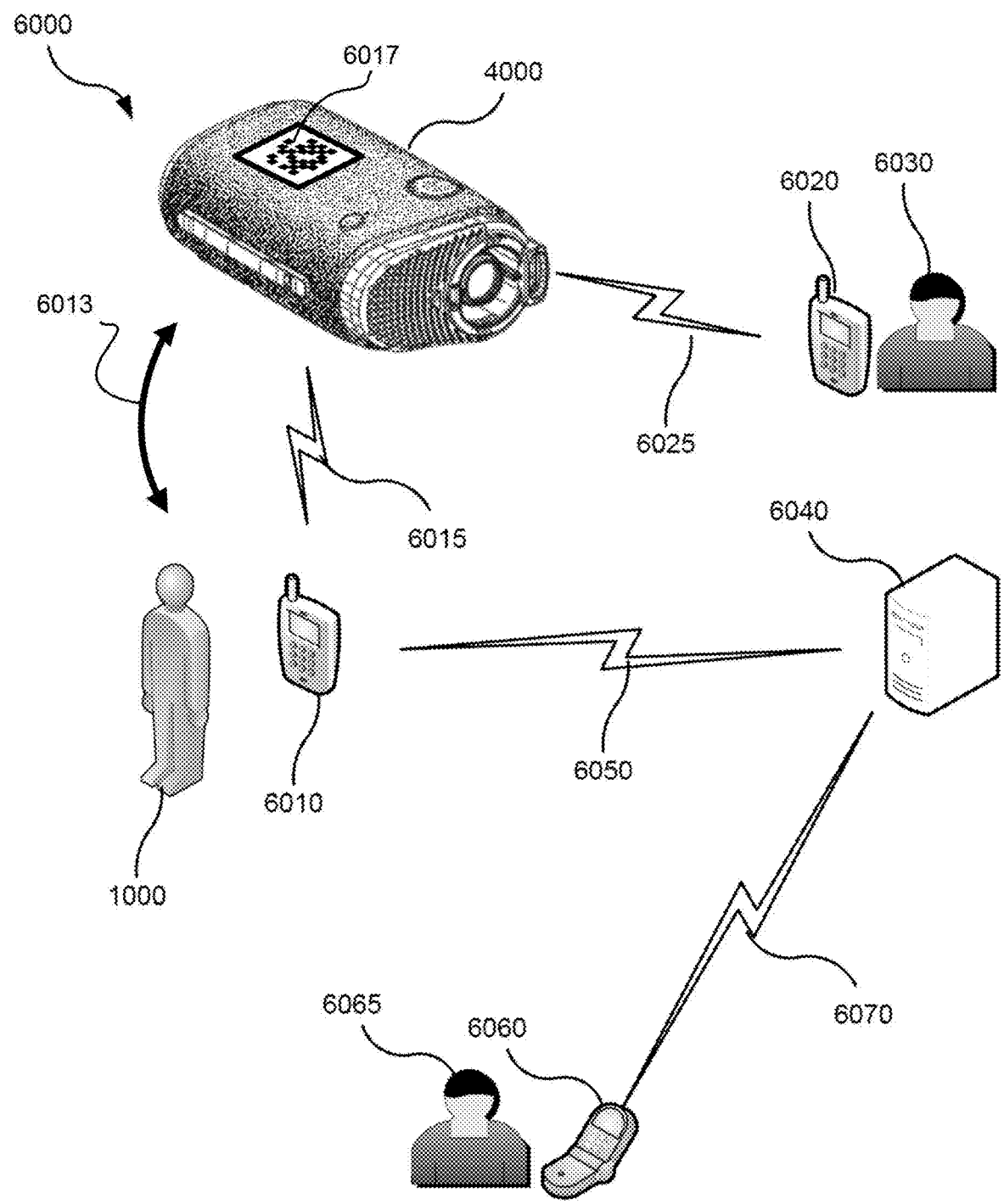

FIG. 6 is a schematic diagram of a networked respiratory therapy system in accordance with one form of the present technology.

Figure 7:
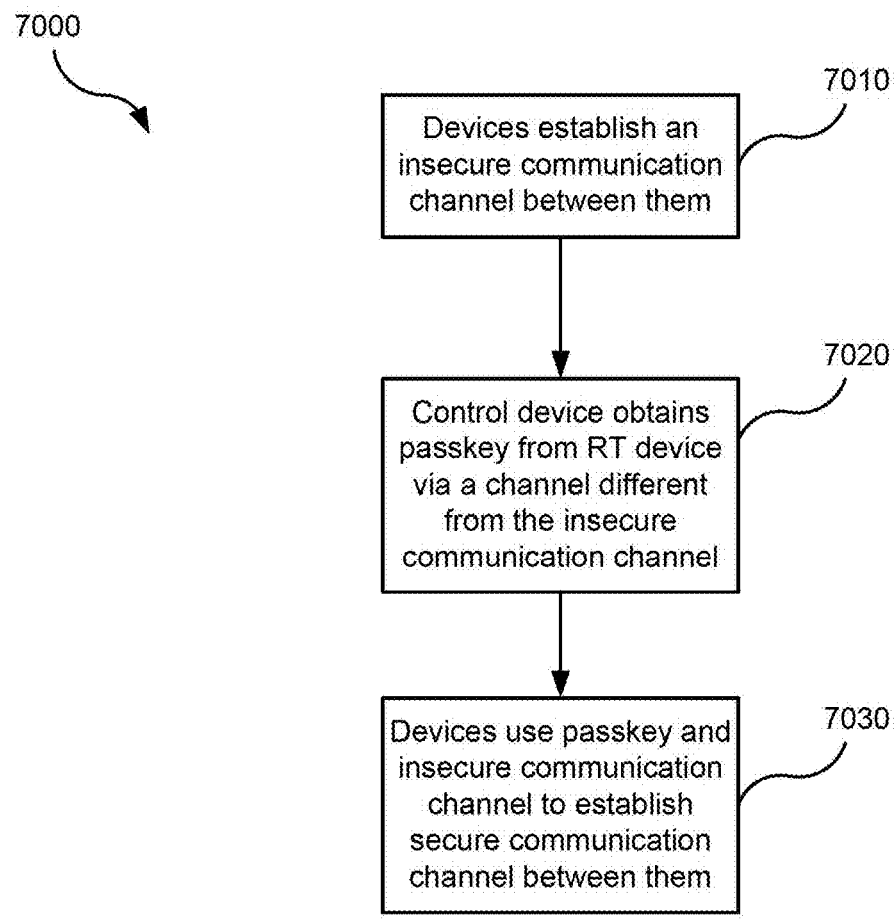

FIG. 7 is a flow chart illustrating a method that may be used by a control device and an RT device of the system of FIG. 6 to establish a secure communication channel between them according to one form of the present technology.

Figure 8:
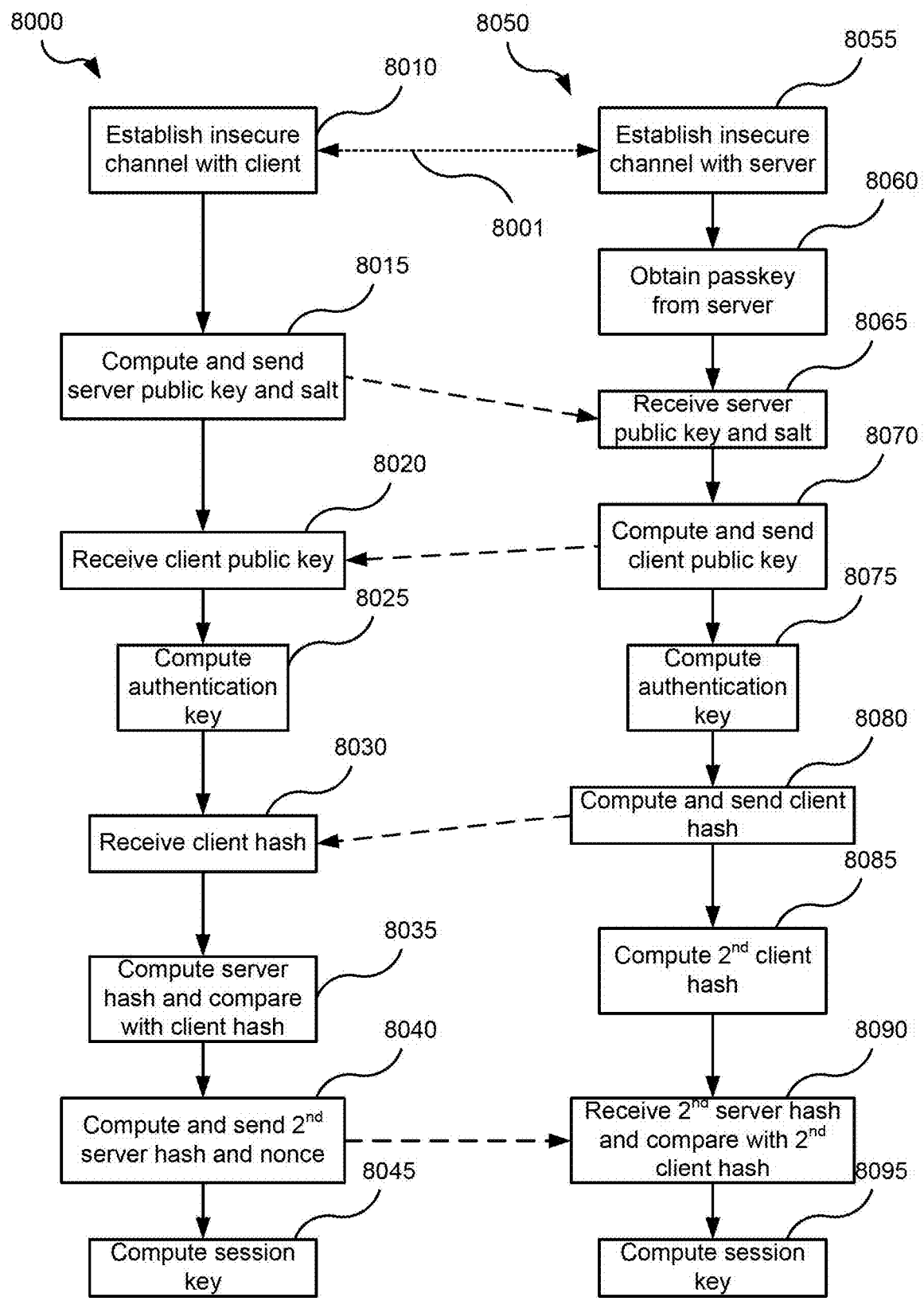

FIG. 8 contains flow charts illustrating methods and that may be carried out by the RT device and control device respectively to implement their respective roles in the method of FIG. 7 according to one form of the present technology.

Figure 9:
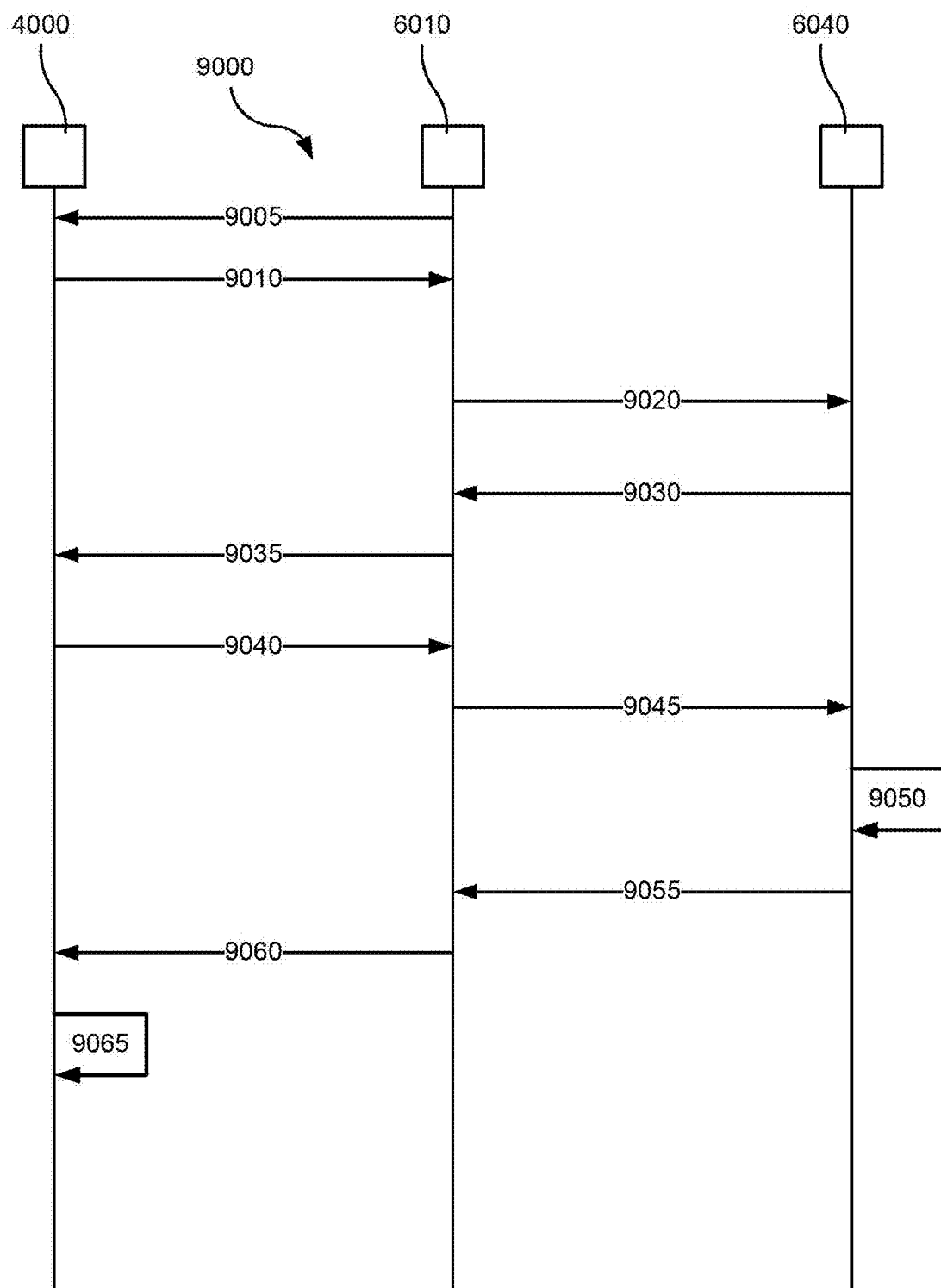

FIG. 9 is a schematic representation of a method that may be implemented by the networked respiratory therapy system of FIG. 6 to secure a firmware upgrade to the RT device according to one form of the present technology.

Figure 10:
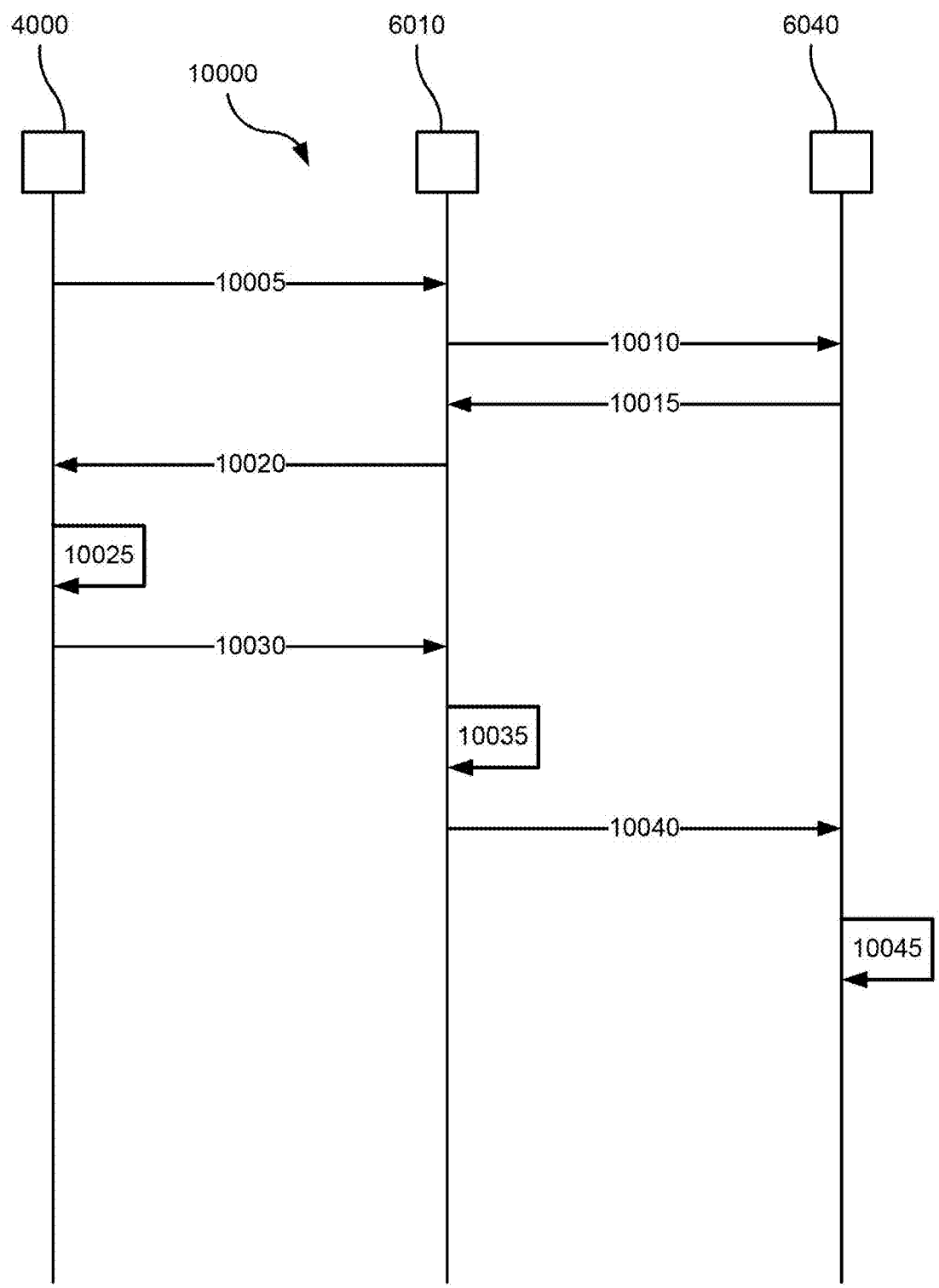

FIG. 10 is a schematic representation of a method that may be implemented by the networked respiratory therapy system of FIG. 6 to authorise a therapy data upload to the server according to one form of the present technology.

Figure 11:
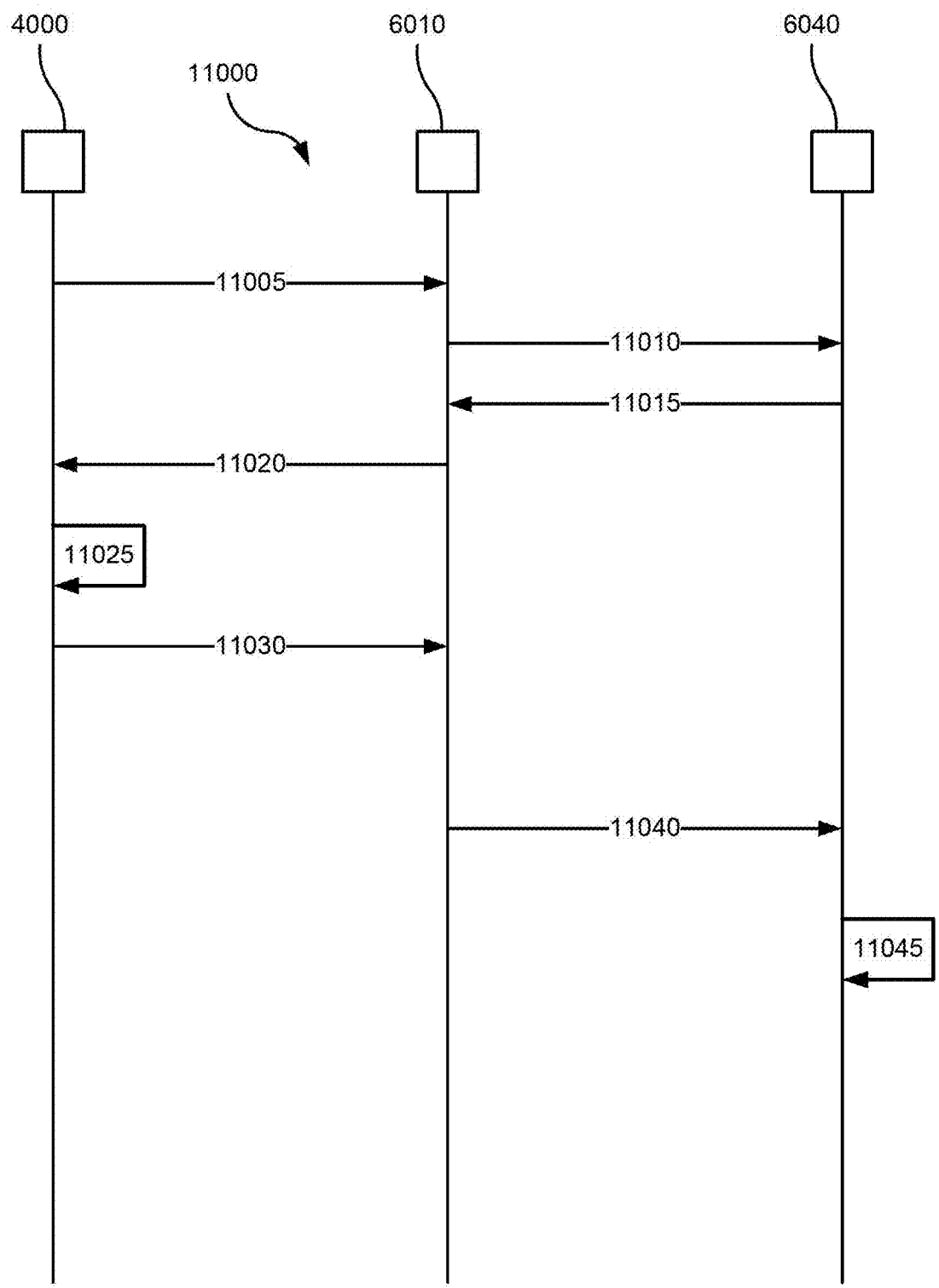

FIG. 11 is a schematic representation of a method that may be implemented by the networked respiratory therapy system of FIG. 6 to authorise a therapy data upload to the server according to another form of the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising supplying a flow of air at positive pressure to the entrance of the airways of a patient 1000.

5.2 Respiratory Therapy System

In one form, the present technology comprises a respiratory therapy system for treating a respiratory disorder. The respiratory therapy system may comprise an RT device 4000 for supplying a flow of air at positive pressure to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 RT Device

An RT device 4000 in accordance with one aspect of the present technology comprises mechanical, pneumatic, and/or electrical components and may be configured to execute one or more algorithms, such as any of the methods, in whole or in part, described herein. The RT device 4000 may be configured to supply a flow of air at positive pressure to an entrance to a patient's airways, such as to treat one or more of the respiratory disorders described elsewhere in the present document.

The RT device may have an external housing 4010, formed in two parts, an upper portion 4012 and a lower portion 4014. Furthermore, the external housing 4010 may include one or more panel(s) 4015. The RT device 4000 comprises a chassis 4016 that supports one or more internal components of the RT device 4000. The RT device 4000 may include a handle 4018.

The pneumatic path of the RT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RT device 4000 may include more than one PCBA 4202.

5.4.1 RT Device Mechanical & Pneumatic Components

An RT device may comprise one or more of the following components in an integral unit. In an alternative form, one or more of the following components may be located as respective separate units.

5.4.1.1 Air Filter(s)

An RT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RT device, or external of the RT device. External transducers may be located for example on or form part of the air circuit, e.g., the patient interface. External transducers may be in the form of non-contact sensors such as a Doppler radar movement sensor that transmit or transfer data to the RT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RT Device Electrical Components

5.4.2.1 Power Supply

A power supply 4210 may be located internal or external of the external housing 4010 of the RT device 4000.

In one form of the present technology, power supply 4210 provides electrical power to the RT device 4000 only. In another form of the present technology, power supply 4210 provides electrical power to both RT device 4000 and humidifier 5000.

5.4.2.2 Input Device

In one form of the present technology, an RT device 4000 includes an input device 4220 to allow a patient to interact with the device. In one such form, the input device 4220 comprises one or more buttons, switches or dials.

5.4.2.3 Central Controller

In one form of the present technology, the central controller 4230 is one or a plurality of processors suitable to control an RT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as one or more algorithms expressed as computer programs or "firmware" stored in a non-transitory computer readable storage medium, such as memory 4260. For example, one algorithm may detect respiratory events of the patient during respiratory therapy.

5.4.2.4 Clock

The RT device 4000 may include a clock 4232 that is connected to the central controller 4230.

5.4.2.5 Therapy Device Controller

In one form of the present technology, therapy device controller 4240 is a therapy control module that forms part of the algorithms executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms mentioned above.

5.4.2.8 Communication

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288. Local external communication network 4284 may be wired or wireless.

In one form, data communication interface 4280 is part of the central controller 4230. In another form, data communication interface 4280 is separate from the central controller 4230, and may comprise an integrated circuit or a processor.

5.4.2.9 Output Device

An output device 4290 in accordance with the present technology may take the form of one or more of a visual, audio and haptic unit. In one form, the output device 4290 may be comprise or more LEDs.

The output device 4290 and the input device 4220 may be collectively referred to as the user interface of the RT device 4000.

5.5 Air Circuit

An air circuit 4170 in accordance with an aspect of the present technology is a conduit or a tube constructed and arranged to allow, in use, a flow of air to travel between two components such as RT device 4000 and the patient interface 3000.

5.6 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Secure Networked Respiratory Therapy

Figure 1:
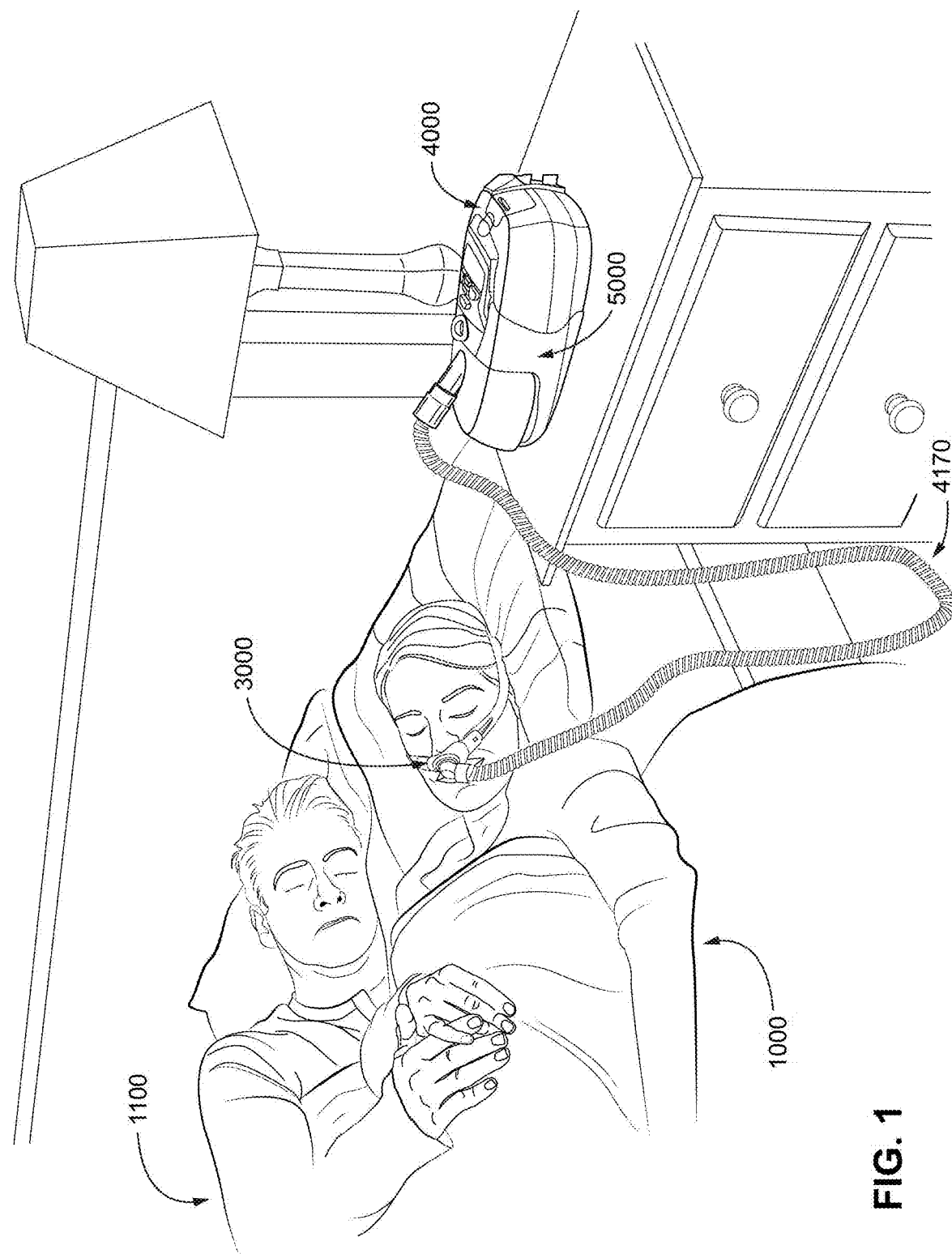
Figure 2:
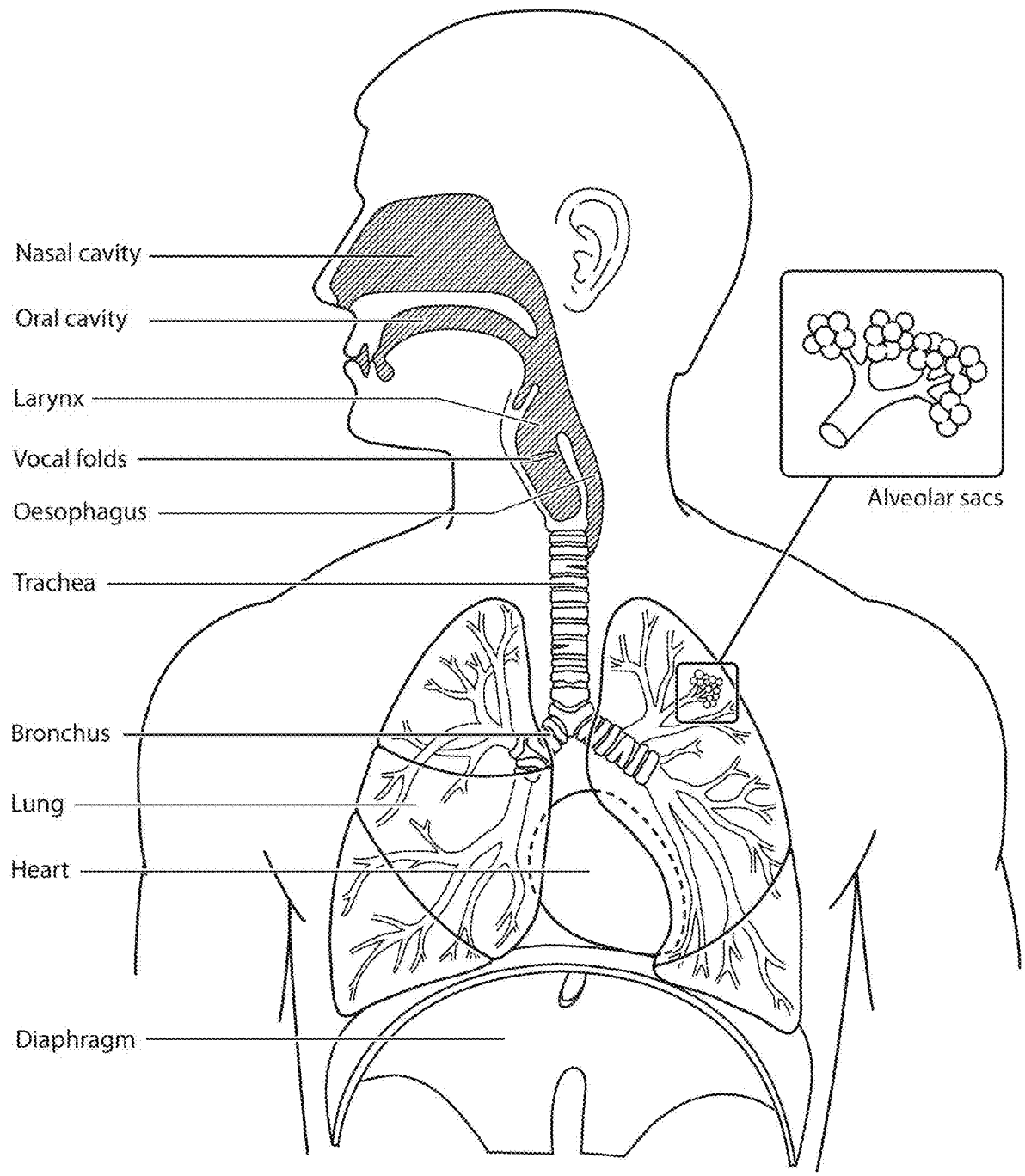
Figure 3:
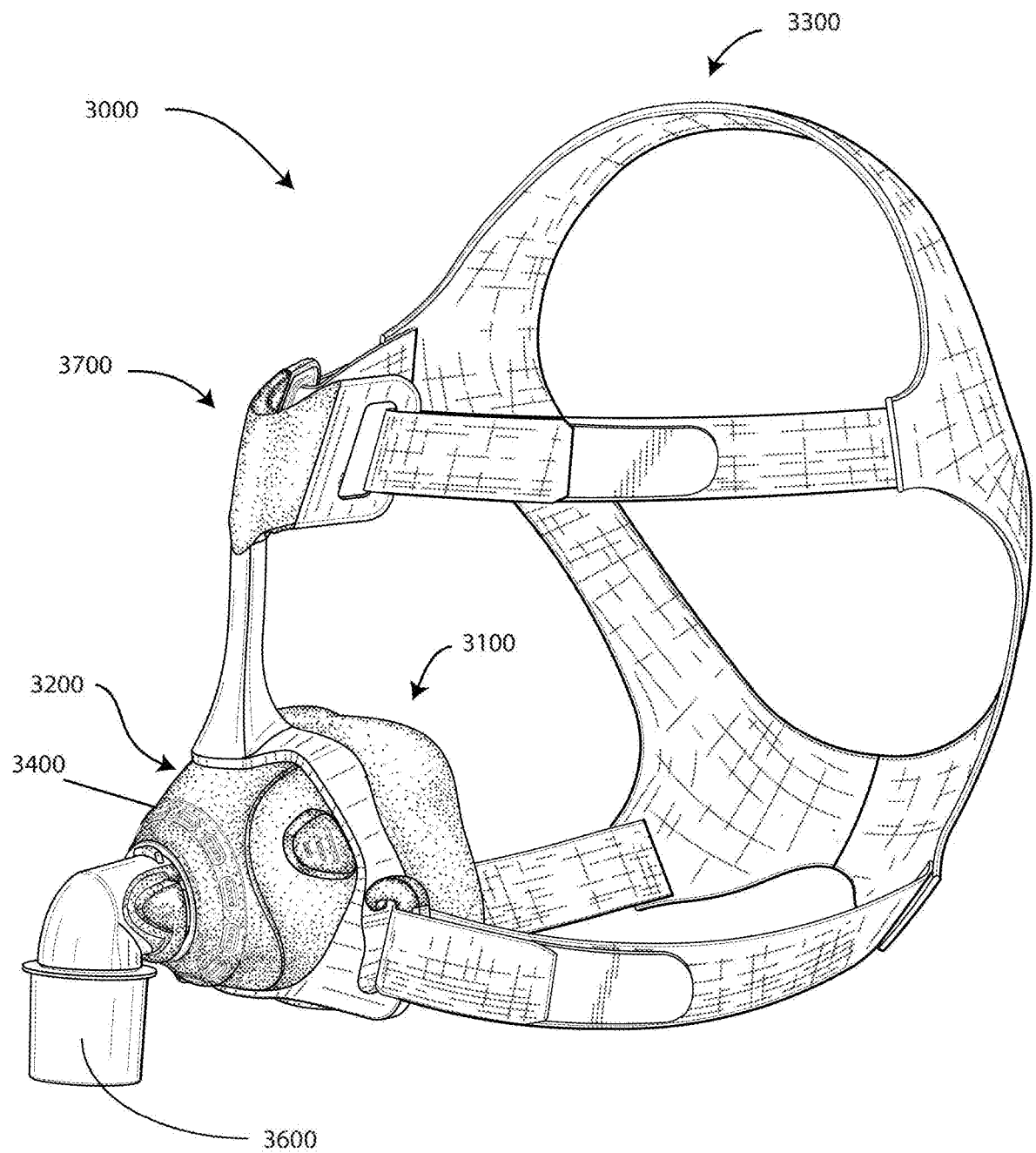

FIG. 6 is a schematic diagram of a networked respiratory therapy system 6000, along with some extraneous entities, in accordance with one form of the present technology. The system comprises an RT device 4000. The RT device 4000 is configured to supply a flow of air at positive pressure to the patient 1000 via an air circuit 4170 to a patient interface 3000 as illustrated in FIG. 1.

Figure 4A:
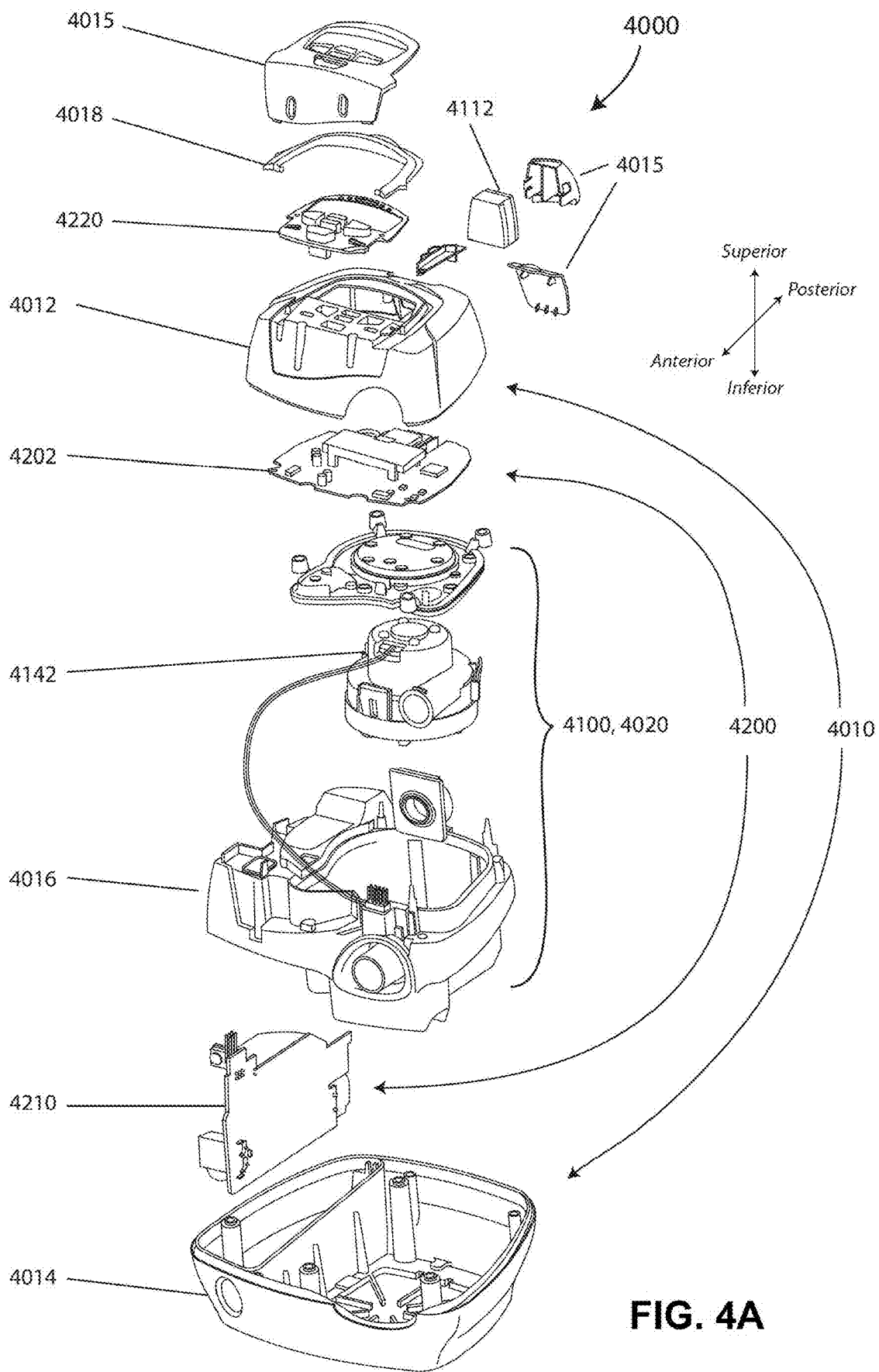
FIG. 4A shows an RT device in accordance with one form of the present technology.
Figure 4B:
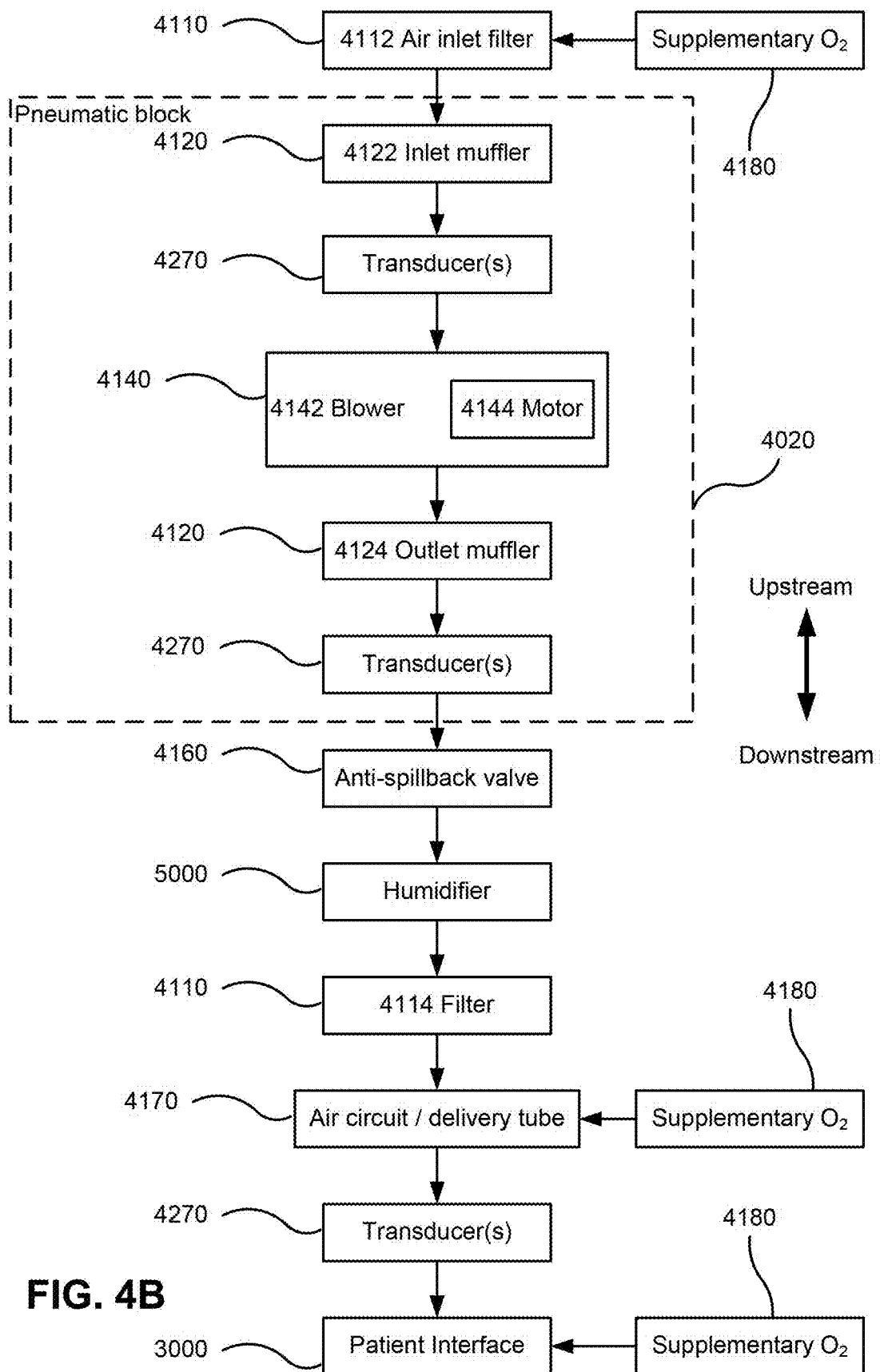
FIG. 4B is a schematic diagram of the pneumatic path of an RT device in accordance with one form of the present technology. The directions of upstream and downstream are indicated.
Figure 4C:
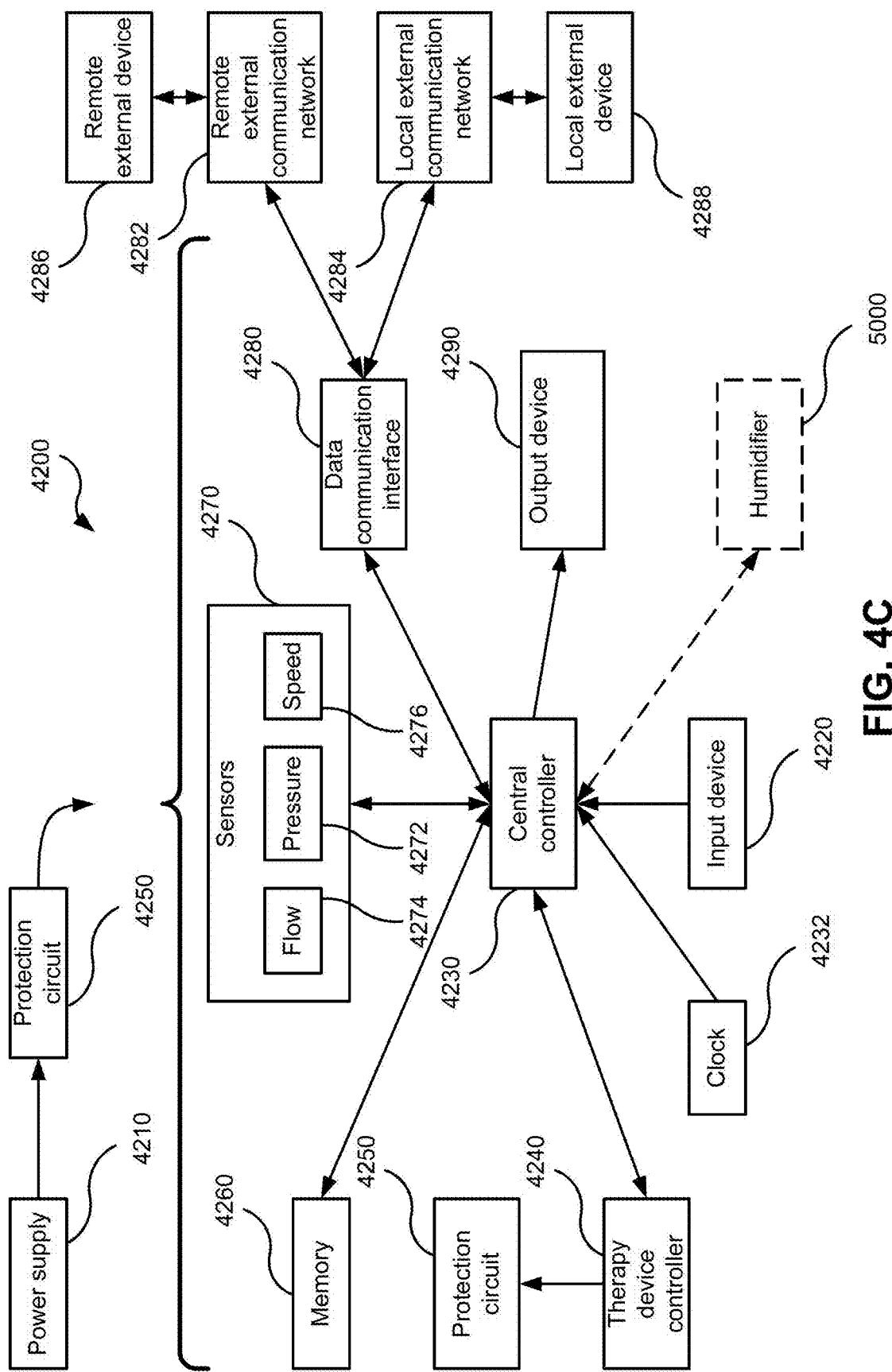
FIG. 4C is a schematic diagram of the electrical components of an RT device in accordance with one form of the present technology.

The RT device 4000 is in communication with a control device 6010 via a wireless connection 6015. The control device 6010 is associated with the patient 1000. The control device 6010 may correspond with the local external device 4288 of FIG. 4C, and the wireless connection 6015 may correspond with the local external communication network 4284. The control device 6010 is a control device for the RT device 4000 such as a dedicated "remote control" or general purpose computing device configured by running a special-purpose software application or "app". Such a software application may be downloaded by the control device 6010 from a server, such as a web server, over a network such as an intranet or the Internet. The control device 6010 may be portable. In some forms, the wireless connection 6015 utilises one or more wireless communication protocols, such as Bluetooth or Bluetooth LE, NFC, or a consumer infrared protocol. Thus, wireless connection 6015 may involve short range or low energy networking, which may be a direct link between the control device and the RT device.

FIG. 6 also illustrates a second control device 6020 in communication with the RT device 4000 via a wireless connection 6025. However, the second control device 6020 does not form part of the respiratory therapy system 6000. If the wireless connection 6025 utilises the same protocol as the wireless connection 6015, there is potential for a malefactor 6030 in possession of the second control device 6020 to compromise the security of the wireless connection 6015 between the control device 6010 and the RT device 4000 via the second control device 6020. For this reason, the second control device 6020 may be referred to as an unauthorised control device 6020. More detail is given below about arrangements to secure the wireless connection 6015 against various threats posed by the unauthorised control device 6020.

The networked respiratory therapy system 6000 also contains a remote server 6040 that is in communication with the control device 6010 via a wireless connection 6050. The remote server 6040 may be accessible to the control device, such as control device 6010, via the wireless connection 6050 over one or more networks such as an internet or the Internet. Thus, the wireless connection 6050 may serve as an indirect networking link to the remote server. Such wireless networking may include for example, WIFI networks, Bluetooth networks, radio cellular networks (e.g., Global System for Mobile Communication (GSM) network etc.). Thus, the wireless connection 6050 may involve long range wireless communications when compared to the wireless connection 6015. The control device 6010 may be configured to act as an intermediary between the RT device 4000 and the remote server 6040. The networked respiratory therapy system 6000 may contain other RT devices (not shown), each controlled by a corresponding control device (not shown), in communication with the server 6040 via corresponding wireless connections (not shown). The server 6040 is therefore configured to serve multiple RT devices 4000 without confusion between them.

The RT device 4000 may be configured to send data relating to the respiratory therapy, e.g. time of usage, number of respiratory events, or compliance rule evaluation results to the control device 6010 via the connection 6015. Such therapy data may in turn be uploaded by the control device 6010 to the server 6040 over the connection 6050. The control device 6010 may be configured to send a control parameter, such as a compliance rule, for the respiratory therapy to the RT device 4000 via the connection 6015. Such a control parameter may be downloaded by the control device 6010 from the server 6040 over the connection 6050. The control device 6010 may also be configured to send an upgrade to the firmware of the RT device 4000 via the connection 6015. Such an upgrade may be downloaded by the control device 6010 from the server 6040 over the connection 6050.

FIG. 6 also illustrates a computing device 6060 in communication with the server 6040 via a wireless connection 6070. However, the computing device 6060 does not form part of the networked respiratory therapy system 6000. In addition, the computing device 6060 is not in communication with an RT device, and is therefore referred to as an unassociated (control) device. If the wireless connection 6070 utilises the same protocol as the wireless connection 6050, and the unassociated device 6060 runs a "spoofed" version of the app that runs on the control device 6010 in order to appear to the server 6040 like a legitimate control device 6010, there is potential for a malefactor 6065 in possession of the unassociated device 6060 to compromise the operation of the networked respiratory therapy system 6000, and in particular the server 6040, via the unassociated device 6060. More detail is given below about arrangements to secure the server 6040 against various threats posed by an unassociated device 6060.

A third category of threat to the networked respiratory therapy system 6000 occurs when the control device 6010 in communication with the RT device 4000 is under the control of a malefactor (not shown). The malefactor has installed on the control device 6010 a "spoofed" version of the app that runs on authorised control devices. The spoofed version attempts to make it appear, for nefarious purposes, to the server 6040 and/or the RT device 4000 like an authorised control device. Such a control device 6010 is therefore referred to as a "spoofed" control device. In other words, the server 6040 cannot be certain that any control device 6010 communicating with it is not "spoofed", and for this reason must treat any control device 6010 in the networked respiratory therapy system 6000 as untrustworthy. More detail is given below about arrangements to secure the server 6040 against various threats posed by such a spoofed control device 6010.

5.7.1 RT Device and Control Device

As mentioned above, it is desirable to prevent security breaches of the wireless communication 6015 between the RT device 4000 and the control device 6010 from the unauthorised control device 6020. It is further desirable to minimise the complexity of establishing a secure communication channel between the control device 6010 and the RT device 4000. Furthermore, the secure communication channel should be establishable using what may be a highly limited user interface on the RT device 4000, whose input device 4220 may consist of one button and whose output device 4290 may consist of one LED. However, the channel establishment method should also be useable on an RT device with a more sophisticated user interface.

A communication channel between two devices may be secured by use of a symmetric key known to both devices, but unknown to other devices, to encrypt and decrypt communications between the devices. The security of the channel is directly related to the cryptographic "strength" of the symmetric key. Strength generally equates to the number of possible key values and the entropy or randomness of the values chosen. In general, for keys where the probability of any value occurring is the same for all possible values, the larger the number of possible values, the higher the entropy and the stronger the key. One difficulty in establishing such a secure channel is in making the symmetric key known to both devices while keeping it secret from unauthorised control devices, e.g. 6020, able to eavesdrop on unencrypted communications between the two devices.

FIG. 7 is a flow chart illustrating a method 7000 that may be used by a control device 6010 and an RT device 4000 to establish a secure communication channel between them according to one form of the present technology. That is, a controller or processor of the control device 6010 and/or the RT device 4000 may be configured to perform the methodologies (e.g., programmed) as described herein such as in relation to FIGS. 7 and 8.

The method 7000 starts at step 7010, at which the control device 6010 and the RT device 4000 establish a communication channel between them. This step may be initiated by activation of some input on the user interface of the RT device 4000, e.g. pressing a button 4220 forming part of the user interface of the RT device 4000. The RT device 4000 may be configured to limit or permit the availability of such an activation input to any one or more of a patient, a clinician or an authorized technician such as a technician of a medical equipment provider. An LED 4290 also forming part of the user interface of the RT device 4000 may flash on and off to indicate that the RT device 4000 is ready to connect to a control device. This initiating action causes any control device currently connected to the RT device 4000 to be disconnected. Thus, an existing control-related communication channel with the RT device 4000 will be terminated by the RT device 4000.

In implementations of the method 7000 in which the wireless protocol to be used is a standard communications protocol, such as Bluetooth, in response to the user initiating action, the RT device 4000 enters a "discoverable" mode, meaning that a device that supports the protocol, e.g., Bluetooth, may pair with the RT device as part of step 7010. In one such implementation, the devices are configured, such as by use of the Just Works association model of the Simple Pairing feature of the Lisbon release of the Bluetooth Core Specification [1], to establish an encrypted communication channel between them by sharing a symmetric key. Each device may then encrypt and decrypt communications with the shared symmetric key. Simple Pairing gives equivalent strength of protection against passive eavesdropping attacks to the pairing in legacy Bluetooth 2.0+EDR (and earlier) when the latter uses a 16-character, case sensitive, alphanumeric PIN (approximately 95 bits of entropy), with the advantage of being much simpler to use. Under the Just Works association model of Simple Pairing, the user does not need to do anything other than accept the pairing by selecting "yes" on a yes/no control on a user interface of the control device 6010. Just Works is particularly suited to RT devices with the simplest of user interfaces consisting of a single button 4220 and LED 4290, since such devices may be unable to display a variable alphanumeric code, as required by the Numeric Comparison association model of Simple Pairing. In other implementations of step 7010, including those where the wireless protocol to be used is Bluetooth, the communication channel established by step 7010 is unencrypted (i.e. it is a "clear" channel).

The result of step 7010 is that both devices have access to a channel for bidirectional communication between them. The LED 4290 may indicate the completion of step 7010 by a steady illumination. If the channel is unencrypted, it is considered insecure due to the risk of passive eavesdropping.

An active unauthorised control device, e.g. 6020, can discover the RT device 4000 while it is in discoverable mode and pair with it via the Just Works association model, thereby denying service to the control device 6010.

To reduce this possibility, in some implementations the effect of the user action that initiates step 7010 may be time-limited, e.g. within a "discoverable window". Under such implementations, the RT device 4000 only makes itself discoverable during the discoverable window, e.g. of duration sixty seconds. Outside the discoverable window, the RT device 4000 is not discoverable by any devices communicating on the standard protocol, e.g., Bluetooth devices. This may be indicated by extinguishment of the LED 4290. This limits the time during which an unauthorised control device, e.g. 6020, attempting denial of service needs to be in communication with the RT device 4000 to a brief interval in which the control device 6010 is also actively trying to pair with the RT device 4000.

If the unauthorised control device 6020 should succeed in pairing with the RT device 4000, this situation is detectable by the control device 6010 since its own pairing fails to complete with a certain predetermined time limit. The control device 6010 may communicate this failure to the user, and prompt the user to repeat the initiating action (e.g. by pressing a button 4220 on the RT device 4000), which as mentioned above disconnects any control device paired with the RT device 4000. In one implementation, the discoverable window may be of longer duration for the second and subsequent attempts at pairing than for the first attempt at pairing.

A more serious threat than denial of service is that the unauthorised control device 6020 during the discoverable window may become a "man in the middle" (MITM), without detection by either device 6010 or 4000. A man-in-the-middle attack occurs when the unauthorised control device 6020 masquerades to each device as the other device in a Bluetooth pairing operation. The unauthorised control device 6020 then relays information between the two devices, giving each the illusion that they are directly paired, and computes the symmetric key. Knowing the symmetric key, the unauthorised control device 6020 may thus eavesdrop on the channel between the two devices and be able to insert and modify information in the channel (this is known as "active eavesdropping"). Thus, even with exchange or sharing of a symmetric key between the RT device 4000 and the control device 6010, the channel established by step 7010 is nevertheless considered insecure with respect to the risk of at least active eavesdropping, even using Just Works Simple Pairing and/or the "discoverable window" option described above.

Returning to the method 7000, once the control device 6010 succeeds in establishing an insecure communication channel with the RT device 4000 in step 7010, the RT device 4000 may make itself no longer discoverable by other devices communicating on the standard protocol. Steps 7020 and 7030 may then be implemented to reduce the risk of passive and active eavesdropping by establishing a first shared secret, such as a token, and converting it, using communications over the insecure channel, into a second shared secret, such as a second more complex token, that is stronger than the first shared secret. The first shared secret cannot be the symmetric key established by step 7010, or derivable from it, since this may be known to an unauthorised control device, e.g. 6020. The aim of step 7020 is therefore to establish a first shared secret using a different channel than the insecure channel established in step 7010.

A common significant difference between the control device 6010 and the unauthorised control device 6020 is that the former has physical access to the RT device 4000 while the latter does not. Step 7020 takes advantage of this difference to establish a first shared secret between the control device 6010 and the RT device 4000. Such a first secret may be predetermined, such as by the manufacturer, so that the first secret may be distributed, such as to the user, with the RT device 4000. Thus, the controller within the RT device 4000 may be pre-programmed for distribution based on the first secret (e.g., with the first secret). Such a first secret becomes shared when obtained for/by the control device 6010. The first secret may be obtained by the control device 6010 via a different channel or medium, for example the channel 6013 in FIG. 6, than the insecure communication channel established between the control device 6010 and RT device 4000 in step 7010. For example, in step 7020 the control device 6010 obtains a token or passkey known to the RT device 4000, via the different channel 6013. The token or passkey may be considered the first shared secret. The passkey may be different and randomised for each RT device 4000 originating from a single manufacturer. The different channel 6013 is sometimes referred to as an "out-of-band" mechanism. Some implementations of step 7020 may take advantage of the physical access of the control device 6010 to the RT device 4000. Other such "different channel" transfers may also be used in step 7020 (e.g., via telephone, mail, user/operations manual, manufacturer website access, other distributed material unique to the particular RT device 4000 such as from the manufacturer, etc.).

In step 7030, the control device 6010 and the RT device 4000 then use the token or passkey and an exchange of information (e.g., a key exchange) over the insecure communication channel to establish a second shared secret. Thus, either or both devices may separately generate the second shared secret from (1) the first shared secret that was not communicated over the insecure channel and (2) the exchanged information that was communicated over the insecure channel. This second shared secret, which may be a more complex token (e.g., having a greater number of bits, digits and/or characters) than the prior token, may be considered to be an "authorisation key". The second shared secret may then be used to derive or generate a symmetric key known as the "session key." Neither the second shared secret nor the session key needs to be exchanged through a communication on the insecure channel. The control device 6010 and the RT device 4000, both in possession of the session key, may then use the session key for communications (e.g., encryption and decryption), thereby establishing a communication channel that is secure relative to the insecure communication channel established in step 7010. Without knowledge of the passkey, an unauthorised MITM control device cannot compute or derive the second shared secret or the session key and hence cannot eavesdrop on the communication channel established during step 7030, even with full knowledge of the data passing back and forth in the insecure communication channel during that step. The unauthorised MITM control device, not knowing the session key, cannot decrypt information encrypted with the session key, nor can it insert intelligible information into the channel. The communication channel established in step 7030 may therefore be considered secure relative to the insecure communication channel established in step 7010.

In one "physical access" implementation of step 7020, the passkey is a token printed on a physical part of the RT device 4000, e.g. the housing 4010, or its user manual/operations manual or other documentation that may be distributed with the RT device 4000. The passkey may be printed in human-readable form, machine-readable form, or both. In one implementation of the machine-readable form, the token may be obfuscated to avoid easy human understanding. For example, one such implementation may be a token that is encoded as a barcode 6017, e.g. a QR code, printed on the housing 4010, or other coded graphic symbol/representation. In such an implementation, the control device 6010 is configured with a barcode reader, e.g. a camera and associated barcode decoding image processing functionality, and in step 7020 the control device 6010 uses the barcode reader to scan the barcode and thus obtain the passkey. In one implementation of the human-readable form, the passkey is printed in alphanumeric form on the housing 4010. In such an implementation of step 7020, the control device 6010 obtains the passkey through manual entry by the user to the user interface of the control device 6010. In one such implementation, the human-readable form of the passkey is a five-decimal-digit numeric code (100 000 possibilities). Such a passkey is "weak" in the sense that it has only approximately 16 bits of entropy. In another implementation, the human-readable form of the passkey is a four-decimal-digit numeric code (e.g., "7409"), which may be considered similarly weak.

As mentioned above, the passkey may be printed on the housing 4010 in both machine-readable and human-readable form. In such an implementation, at step 7020 the control device 6010 first attempts to scan the machine-readable form of the passkey into the control device 6010. If that fails, the control device 6010 prompts the user to manually enter the human-readable form of the passkey through the user interface of the control device 6010.

In another "physical access" implementation of step 7020, the control device 6010 obtains the token from the RT device 4000 via a close-range wireless protocol such as near-field communication (NFC). In another "physical access" implementation of step 7020, the control device 6010 obtains the token from the RT device 4000 by scanning an RFID tag embedded in the RT device 4000, the RFID tag encoding the token.

At step 7030, both devices jointly implement a key exchange protocol by communicating over the insecure channel to compute a shared (symmetric) authorisation key. The passkey (the first shared secret) obtained at step 7020 is used in step 7030 to authenticate the key exchange. In some implementations of step 7030, a Diffie-Hellman-based key exchange protocol may be used such as the Secure Remote Password (SRP) Protocol. In one implementation of step 7030, a variant of a Diffie-Hellman-based protocol known as SRP6a [2] is used. SRP6a has the following properties:

Safety against eavesdropping. The passkey is never sent over the insecure communication channel, either in the clear or encrypted.

Immunity to replay attacks. Re-use of captured information to gain access is prevented.

Resistance to offline dictionary attack. Capturing traffic does not reveal any information for an offline computational attack.

Forward security. If the passkey becomes known, traffic captured with past sessions remains safe from decryption.

Does not require a backend connection over which certificates can be passed for authentication.

As mentioned above, SRP6a achieves security through a Diffie-Hellman-based round of calculations. Under SRP6a, one device (in the present technology the RT device 4000) is designated as the server, the other (the control device 6010) as the client. The server (authenticator) converts the shared passkey into a verifier which it then combines with a Diffie-Hellman exponentiation to generate a public key. This allows security to be retained when used with low-entropy passkeys such as a five-digit passkey. The client (peer) also generates a Diffie-Hellman style public key. The public keys are exchanged over the insecure channel and from that information both the client and server calculate a shared secret (the authorisation key) that is stronger than the passkey. Optionally, the two devices may then perform a finished message confirmation sequence to prove to themselves that their calculated authorisation keys are identical. This is accomplished through a sequence of hashes, the results of which are exchanged between the devices and compared. If either comparison fails, step 7030 is aborted, as this is evidence that an MITM control device is attempting to participate in the key exchange using an incorrectly guessed passkey. For added security, in preferred implementations of step 7030, the authorisation key should be statistically unlikely to be the same if step 7030 is repeated with the same passkey.

Both devices store a hash of the authorisation key in secure persistent storage (e.g. the memory 4260 for the RT device 4000). As mentioned above, in a final sub-step of step 7030, each device computes a session key from the hash of the authorisation key for encryption/decryption during the current session. The session key computation may also be based on a single-use random number called a "nonce" that is generated and sent from one device to the other device. In one implementation, the "nonce" is a random number that is generated by the server and is sent to the client over the insecure communication channel, used by both devices in the session key computation, and then discarded. This sub-step, with a different nonce, may be repeated at each subsequent re-pairing of the devices to compute a different session key for each communication session, thereby enabling the "forward security" mentioned earlier.

The passkey itself need not be stored in the memory 4260 of the RT device 4000. Instead, a hash of the passkey may be stored in the memory 4260, as this is all that is needed on the server side to perform step 7030 according to SRP6a. The passkey hash is inaccessible externally to the RT device 4000, in that no access is offered via the interface 4280 to external computing devices, local or remote, to the locations in memory 4260 where the hash is stored. The passkey need not be stored by the control device 6010 once step 7030 is completed, as it is not used in subsequent re-pairing operations.

FIG. 8 contains two flow charts illustrating methods 8000 and 8050 that may be carried out by the server (RT device 4000) and client (control device 6010) respectively to implement their respective roles in the method 7000 according to one form of the present technology.

The method 8000 starts at step 8010, and the method 8050 starts at step 8055, at which the server and the client respectively take the actions necessary to establish an insecure communication channel with each other using, for example, Just Works Simple Pairing of the Bluetooth protocol (step 7010). These steps require insecure bidirectional communication between the two devices, as indicated by the bidirectional dotted arrow 8001. The remaining communications between the two devices, indicated by the dashed arrows between methods 8000 and 8050, excepting the communication in step 8060, take place over the insecure communication channel.

Step 8060 of the method 8050 follows, at which the client obtains a passkey (P), or first shared secret, from the server such as using its physical access to the server, as described above in relation to step 7020. The remaining steps of the methods 8000 and 8050 implement step 7030 of the method 7000. At step 8015 of the method 8000, the server computes a server public key (B) using a salt (s). The salt (s) is a random number generated by the server. Diffie-Hellman key exchange is based on a multiplicative group of integers modulo a large prime number (N) known as the group prime. To compute the server public key (B), the server uses a group generator (g), which is a small integer, e.g. 2, and the group prime (N). The server first computes an exponent (x) as a hash of the salt (s) concatenated with a hash of the passkey (P):

$$x = \text{HASH}(s|\text{HASH}(P))$$

where "|" indicates concatenation. One example of a hash function is a function known as SHA256. The server then computes a verifier (v) by raising the group generator (g) to the exponent (x) modulo the group prime (N) as follows:

$$v = g^x \bmod N$$

The server then computes a multiplier (k) by hashing the group prime (N) and the group generator (g):

$$k = \text{HASH}(N|\text{PAD}(g))$$

where PAD( ) indicates a padding function intended to bring its argument to the length required by the hash function. PAD( ) may merely append zeros to its argument, but other implementations of padding may be used.

The server then computes the server public key (B) as follows:

$$B = k \times v + g^b \bmod N$$

where b is a server random exponent. Step 8015 then sends the server public key (B) and the salt (s) to the client.

Although the aspects of step 8015 may be performed after step 8010 and/or during the communications process, in some cases, the public key or the salt may be computed prior to such communications (e.g., prior to step 8010) so that they may be accessed for sending in step 8015.

The client receives the server public key (B) and the salt (s) at step 8065 of the method 8050. The client knows the group generator (g) and the group prime (N), and at step 8070 is therefore able to compute a client public key (A) by raising the group generator (g) to a client random exponent (a) modulo the group prime (N):

$$A = g^a \bmod N$$

Also in step 8070, the client sends the client public key (A) to the server, which the server receives at step 8020 of the method 8000. Note that steps 8065 and 8070 may be carried out in any order as the client public key (A) is not dependent on the server public key (B) or the salt (s). If step 8070 precedes step 8065, then step 8020 may precede step 8015.

Note also that step 8060 may follow steps 8065 and 8070 since the client does not need the passkey (P) to compute the client public key (A). However, in some cases step 8060 may precede step 8055.

At step 8025 the server computes a hash (u) of the client and server public keys (A and B):

$$u = \text{HASH}(\text{PAD}(A)|\text{PAD}(B))$$

and then computes the second shared secret, or authorisation key (S), from the hash (u), the server random exponent (b), the verifier (v), and the client public key (A) as follows:

$$S = (A \times v^u)^b \bmod N$$

At step 8075 of the method 8050, the client computes the hash (u), the multiplier (k), and the exponent (x) using the above equations (note computing the exponent (x) requires the passkey (P) obtained in step 8060). The client then computes the authorisation key (S) as follows:

$$S = (B - (k \times g^x \bmod N))^{a+ux} \bmod N$$

It may be shown using modulo N arithmetic that the client and the server compute the same authorisation key (S) at steps 8025 and 8075 respectively. However to guard against error or corruption, the subsequent steps of the methods 8000 and 8050 confirm to the server and the client respectively that they share a common authorisation key (S). At step 8080 of the method 8050, the client computes a client hash value (Mclient) as follows:

$$M\text{client} = \text{HASH}(\text{HASH}(g) \text{XOR } \text{HASH}(N)|s|A|B|\text{HASH}(S))$$

and sends the client hash value (Mclient) to the server. The server receives the client hash value (Mclient) at step 8030 of the method 8000. The server then at step 8035 computes a server hash value (Mserver) as follows:

$$M\text{server} = \text{HASH}(\text{HASH}(g) \text{XOR } \text{HASH}(N)|s|A|B|\text{HASH}(S))$$

and compares the server and client hash values (Mserver and Mclient). If they are not equal, the method 8000 aborts and the user is informed of the failure of the secure channel establishment step 7030, e.g. via a user interface of the control device 6010 and/or the output device 4290 of the RT device 4000.

Assuming the server and client hash values (Mserver and Mclient) are equal, the method 8000 continues to step 8040 at which the server computes a second server hash value (HAMKserver) as follows:

HAMKserver=HASH(*A*|Mserver|HASH(*S*))

Also at step 8040, the server sends the second server hash value (HAMKserver) and a nonce (chosen randomly by the server) to the client. Meanwhile at step 8085 of the method 8050, the client computes a second client hash value (HAMKclient) as follows:

HAMKclient=HASH(*A*|Mclient|HASH(*S*))

At step 8090 the client receives the second server hash value (HAMKserver) and the nonce, and compares the second server and client hash values (HAMKserver and HAMKclient). If they are not equal, the method 8050 aborts and the user is informed of the failure of the secure channel establishment step 7030, e.g. generating user output via a user interface of the control device 6010 and/or the output device 4290 of the RT device 4000.

Assuming the second server and client hash values (HAMKserver and HAMKclient) are equal, the method 8050 continues to step 8095 at which the client computes a session key (Ks) by hashing the hash of the authorisation key (S) and the nonce received at step 8090:

*Ks*=HASH(HASH(*S*)|nonce)

Meanwhile, at step 8045 of the method 8000, the server computes the session key (Ks) in the same fashion.

By means of the above-described arrangements, the connection between the control device 6010 and the RT device 4000 may be regarded as secure, in the sense that the chance of an unauthorised control device 6020 actively or passively eavesdropping on the connection 6015 is greatly reduced.

However, even if the connection 6015 between the control device 6010 and the RT device 4000 is secure in this sense, and the connection 6050 between the control device 6010 and the server 6040 is also nominally "secure" (e.g. follows the SSL connection protocol), there still remain the threats to the networked respiratory therapy system 6000 posed by an unassociated control device 6060 and a spoofed control device 6010 as described above.

5.7.2 Control Device and Server

Each RT device, e.g. 4000, in the networked respiratory therapy system 6000 may be identified by a unique identifier that is known to itself and to the server 6040. In addition, each RT device 4000 knows a unique block of data that is known by no other device except the server 6040, where it is securely stored associated with the RT device 4000 by its unique identifier. This block of data is referred to as the RT device's secret. The secret makes possible the security arrangements between the RT device 4000 and the server 6040, since it is unknown to the control device 6010 that intermediates between the RT device and the server 6040, even if the control device 6010 is a spoofed control device.

5.7.2.1 Firmware Upgrade

As mentioned above, the firmware of the RT device 4000 may require upgrading from time to time. If a spoofed control device 6010 can tamper with the upgrade without detection by the RT device 4000, it may be able to alter the operation of the RT device 4000, rendering it ineffectual for respiratory therapy. It would therefore be beneficial for the RT device 4000 to be able to verify that the firmware upgrade originates from the server 6040, is intended for the RT device 4000, and has not been tampered with by the control device 6010.

FIG. 9 is a schematic representation of a method 9000 that may be implemented by the networked respiratory therapy system 6000 to authenticate a firmware upgrade to the RT device 4000. The three entities involved in the method 9000 (the RT device 4000, the control device 6010, and the server 6040) are represented from left to right as respective vertical lines, and the communications between them and other actions are represented as arrows that are sequenced in time from top to bottom.

The method 9000 may start at step 9005, at which the control device optionally 6010 queries the RT device 4000 for its current firmware version number. The RT device 4000 replies to the control device 6010 at step 9010 with its firmware version number. At step 9020, the control device 6010 asks the server 6040 for a firmware upgrade, passing the current firmware version number. The server 6040 responds at step 9030 by sending a firmware upgrade file to the control device 6010, if one is requisite, based on the firmware version number (if no upgrade is available, the server responds with a "none" message which causes the control device 6010 to terminate the method 9000 after step 9030).

In some versions, the method may start at step 9020. In a variation of the method 9000, steps 9005 to 9020 are omitted, and the method 9000 starts at step 9030 at which the server 6040 sends a firmware upgrade file to the control device 6010 based on its own records of the upgrade history of the RT device 4000.

In a further variation of the method 9000, step 9005 requests the RT device's unique identifier rather than its firmware version number. The RT device 4000 replies to the control device 6010 at step 9010 with its unique identifier. At step 9020, the control device 6010 asks the server 6040 for a firmware upgrade, passing the unique identifier. The server 6040 responds at step 9030 by sending a firmware upgrade file to the control device 6010, if one is requisite, based on the unique identifier. Such a variation allows the server 6040 to target specific devices for a firmware upgrade, rather than all devices with a certain firmware version number.

At the next step 9035, the control device 6010 sends the upgrade file to the RT device 4000. At step 9040, the RT device 4000 sends its unique identifier to the control device 6010. (In the further variation mentioned above, step 9040 is not needed as the control device 6010 already knows the unique identifier of the RT device 4000.) Step 9045 follows, at which the control device 6010 requests an authorisation code for the upgrade from the server 6040, passing the unique identifier of the RT device 4000. Step 9050 follows, at which the server 6040 obtains a key from the secret associated with the unique identifier received from the control device 6010, i.e. the secret that is shared with the RT device 4000. In one implementation, the key is a subset of data from the secret. The server 6040 then uses the key to derive an authorisation code from the upgrade file sent to the control device 6010 at step 9030. In one implementation of step 9050, the authorisation code is a Hashed Message Authorisation Code (HMAC) derived from a hash of the upgrade file. In another implementation, the authorisation code is a hash of the upgrade file, encrypted using the key. The use of the hash of the upgrade file, rather than the upgrade file itself, is advantageous for the server 6040 since it is likely to need to perform the same computation multiple times for different RT devices in the networked respiratory therapy system 6000 more or less simultaneously.

The server 6040 at step 9055 then sends the authorisation code to the control device 6010. At step 9060, the control device 6010 sends the authorisation code to the RT device 4000. At step 9065, the RT device 4000 derives a key from its secret in the same manner as the server 6040 at step 9050. The RT device 4000 then (also at step 9065) computes an authorisation code from the upgrade file received from the control device 6010 at step 9035 using the derived key in the same manner as the server 6040 at step 9050. Thus, the computation of the authorisation code by the RT device 4000 at step 9065 mimics the computation performed by the server 6040 at step 9050. The RT device 4000 then compares the computed authorisation code with the authorisation code received at step 9060. If the two codes match, the RT device 4000 has authenticated the upgrade file. The RT device 4000 may then safely apply the upgrade file to its own firmware.

The manner of computing the authorisation code is such that neither the secret nor the key can be derived from the upgrade file and the authorisation code, even if the manner of computing the authorisation code from the upgrade file is known. Furthermore, any tampering with the upgrade file by a spoofed control device 6010 will cause the authorisation code computed by the RT device 4000 at step 9065 to differ from that received from the server 6040 at step 9055. Therefore, because neither the key nor the secret is ever passed to the control device 6010, nor can they be derived by the control device 6010, a spoofed control device 6010 cannot provide a fake or tampered upgrade to the firmware of the RT device 4000, because the control device 6010 cannot compute the expected authorisation code without the key.

5.7.2.2 Therapy Data Upload

As mentioned above, RT devices, e.g. 4000, in the networked respiratory therapy system 6000 may be configured to upload therapy data via their control devices 6010 to the server 6040. A spoofed control device 6010 or an unassociated control device 6060 under the control of a malefactor 6065 may attempt to upload fake or tampered therapy data to the server 6040. This may be regarded as an acceptable risk as little harm to an overall networked therapy system 6000 containing a large number of RT devices can result from an isolated source of fake therapy data. However it is not acceptable for a spoofed control device 6010 or an unassociated control device 6060 to impersonate control devices for other RT devices in the system 6000 and upload fake therapy data purporting to come from those RT devices, since this can potentially swamp the genuine therapy data being uploaded at the server 6040 from authorised control devices 6010. It is therefore desirable that, at around the time of the upload, the control device 6010 be in communication with the RT device 4000 from which it is purporting to upload therapy data. This precondition prevents both impersonation and large-scale uploading of fake therapy data by an unassociated control device 6060 that managed to connect at least once in the past with an RT device 4000 that is subsequently connected with an authorised control device 6010.

FIG. 10 is a schematic representation of a method 10000 that may be used by the networked respiratory therapy system 6000 of FIG. 6 to authorise a therapy data upload to the server according to one form of the present technology.

The method 10000 may start at step 10005, at which the RT device 4000 sends therapy data to the control device 6010. This step may occur at other times relative to the method 10000 but needs to occur prior to transfer of the therapy data to the server. At step 10010, the control device 6010 requests a "nonce" and an offset from the server 6040, passing the identifier of the RT device 4000. A nonce is a (pseudo-)random number with a finite duration, governed either by time and/or number of uses. In this regard, the nonce "expires" after a predetermined time and/or predetermined number of uses. When it expires, the nonce is no longer used by the server 6040. For example, a nonce may have a duration of exactly one use. At step 10015, the server 6040 provides the control device 6010 with a nonce and an offset. The server 6040 keeps track of the number of uses or elapsed time since the nonce was first sent at step 10015, along with the identifier of the RT device 4000, so that the server 6040 can later determine whether the nonce has expired. The offset is a pointer that may be used to derive a key from the secret associated with the identifier received at step 10010, i.e. the secret that is known to the RT device 4000. For example, the pointer may be an identifier for selecting a subset of data from the secret for use as a key or undergoing a hash to generate a key from the subset of data.

Step 10020 follows, at which the control device 6010 asks the RT device 4000 for a signing key, passing the offset and the nonce received from the server at step 10015. At step 10025, the RT device 4000 uses the offset, the nonce, and its secret to derive a signing key. At the next step 10030, the RT device 4000 sends the signing key to the control device 6010. The control device 6010 at step 10035 uses the signing key to obtain an authorisation code for the therapy data. In one implementation, the authorisation code is an HMAC. For example, the authorisation code may be a hash computed with the therapy data and signing key using a cryptographic hash function. At step 10040, the control device 6010 sends the therapy data, the authorisation code, and the identifier of the RT device 4000 to the server 6040. Finally, at step 10045, the server 6040 checks whether the nonce sent at step 10015 associated with the received identifier has expired. If it has, the authorisation fails. If it has not, the server 6040 uses the offset and the nonce sent at step 10015 and the secret associated with the identifier (i.e. the secret that is known to the RT device 4000) to derive a signing key, which it uses to compute an authorisation code for the therapy data. The manner of deriving the signing key and computing the authorisation code are the same as those used by the RT device 4000 and the control device 6010 at steps 10025 and 10035. If there is a match between the computed authorisation code and the authorisation code received at step 10040, the therapy data is authenticated.

Although not shown in FIG. 10, based on such authentication, the server 6040 may then optionally perform operations with the therapy data. For example, the server 6040 may store the therapy data in a therapy-related database for later use. In some cases, the server 6040 may perform a compliance process such as including an evaluation of therapy data such as by applying a compliance rule and/or reporting compliance as previously described.

In subsequent uploads of new therapy data received from the RT device 4000, the control device 6010 may omit the step 10010 and re-use the signing key received at step 10030 of a previous execution of the method 10000. However, if the nonce has expired, and the upload is consequently unauthorised, the control device 6010 will need to re-initiate the method 1000 from step 10010 onwards in order to upload the therapy data. In such a case, the server 6040 may optionally send an error message to prompt such re-initiation.

The connection between the control device 6010 and the server 6040 is not secure, so an unassociated control device 6060 can eavesdrop on step 10015 to obtain the offset and the nonce. However, because the connection between the RT device 4000 and the control device 6010 is secure, the unassociated control device 6060 cannot eavesdrop on that connection to obtain a signing key, and so cannot authorise fake therapy data it may upload to the server 6040. In addition, a control device 6010 that was connected to an RT device 4000, and was therefore able to obtain a signing key once, cannot continue to use the same signing key indefinitely, because the nonce the server 6040 is using to derive the signing key will eventually expire. Furthermore, a spoofed control device 6010 cannot deduce the secret from any number of signing keys, nonces, and offsets, and therefore cannot derive future signing keys itself, no matter how often it participates in the method 10000. A control device 6010 therefore needs to be connected to an RT device 4000 from time to time in order to continue to be able to authorise therapy data uploads. The shorter the duration of the nonce, the closer in time the upload of therapy data must be to the time of connection between the control device 6010 and the RT device 4000, so the security is heightened. However, the computational load on the system 6000 will also be greater, and the convenience of independent operation of control device 6010 and RT device 4000 lessened. It also creates a greater coupling dependence between the RT device 4000 and control device 6010, whereas greater independence between them is desirable. Thus, the expiration duration of the nonce can be chosen to balance such concerns.

In a variation of the method 10000, the offset is not used. In such a case, the RT device 4000 and the server 6040 derive the signing key from the secret and the nonce alone.

Note that the method 10000 does not prevent a spoofed control device 6010 connected with an RT device 4000 from tampering with or faking therapy data before signing it (i.e., computing the authorization code). As such, the server 6040 using the method 10000 will be unable to detect such tampering or faking.

FIG. 11 is a schematic representation of a further method 11000 that may be used by the networked respiratory therapy system 6000 of FIG. 6 to authorise a therapy data upload to the server according to one form of the present technology. The steps 11005 to 11020 of the method 11000 are the same as those of the correspondingly numbered steps 10005 to 10020 of the method 10000.

At step 11025, the RT device 4000 uses the offset, the nonce, and its secret to obtain a signing key. The RT device 4000 then uses the signing key to compute an authorisation code, e.g. an HMAC, from the therapy data sent at step 11005. At step 11030, the RT device 4000 sends the authorisation code to the control device 6010. Step 11040 follows, at which the control device 6010 sends the therapy data, the authorisation code, and the RT device identifier to the server 6040. Finally, at step 11045, the server 6040 checks whether the nonce sent at step 11015 has expired. If it has, the authorisation fails. If it has not, the server 6040 uses the offset and the nonce sent at step 11015 and the secret associated with the RT device identifier (i.e. the secret that is known to the RT device 4000) to derive a signing key. The server 6040 then uses the signing key to compute an authorisation code for the therapy data. The manner of deriving the signing key and computing the authorisation code are the same as that used by the RT device 4000 at step 11025. If there is a match between the computed authorisation code and the authorisation code received at step 11040, the therapy data is authenticated.

Using the method 11000, neither the secret nor the signing key is ever passed to the control device 6010. Furthermore, the manner of deriving the signing key and the authorisation code is such that the signing key cannot be derived from the offset, the nonce, the authorisation code, and the therapy data even if the manner of deriving the signing key and the authorisation code is known to the control device 6010. A spoofed control device 6010 therefore cannot tamper with or fake therapy data without detection by the server 6040 as it does not have a key to generate an authorisation code for the tampered or fake data.

A disadvantage of the method 11000 is the extra computational load and/or storage capacity required on the RT device 4000, which must either sign and send many small chunks of therapy data, or accumulate a large amount of therapy data in memory before signing it and sending it to the control device 6010. In addition, there is a clerical burden on the control device 6010, which may not be simultaneously connected to the server 6040 and the RT device 4000. The control device 6010 therefore needs to keep track of each chunk of therapy data and its associated authorisation code received from the RT device 4000 while disconnected from the server 6040 in order to later forward the therapy data to the server 6040 in association with the correct authorisation codes when the control device 6010 becomes connected to the server 6040.

In a variant of the method 11000, neither the offset nor the nonce is used. In such a case, a signing key derivable from the secret without needing any exchanged information is used by both the RT device 4000 and the server 6040. In one example of such a variant, the signing key is the secret itself. This variant omits steps 11005 to 11020, starting at step 11025 at which the RT device 4000 derives the signing key from the secret and uses it to compute the authorisation code from the therapy data. At step 11030 the RT device sends both the therapy data and the authorisation code to the control device 6010 at step 11030. Step 11040 follows, at which the control device 6010 sends the therapy data and the authorisation code to the server 6040. Finally, at step 11045, the server 6040 uses the secret associated with the identifier (i.e. the secret that is known to the RT device 4000) to derive a signing key, which it uses to compute an authorisation code for the therapy data. The manner of deriving the signing key from the secret and computing the authorisation code are the same as that used by the RT device 4000 at step 11025. If there is a match between the computed authorisation code and the authorisation code received at step 11040, the therapy data is authenticated. Such a variant may be less desirable (weaker security) compared to the method 10000 with its use of a random nonce because its authorization code is essentially derived from a fixed key.

This variant of the method 11000 is potentially less secure than the original method 11000, since one breach of the RT device 4000 by a spoofed control device 6010 or an unassociated control device 6060 would allow such a device to upload any amount of fake therapy data purporting to come from the RT device 4000 to the server 6040.

5.8 Glossary

For the purposes of the present technology disclosure, in certain forms of the present technology, one or more of the following definitions may apply. In other forms of the present technology, alternative definitions may apply.

Air: In certain forms of the present technology, air may be taken to mean atmospheric air, and in other forms of the present technology air may be taken to mean some other combination of breathable gases, e.g. atmospheric air enriched with oxygen.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory disorder of a patient.

Patient: A person, whether or not they are suffering from a respiratory disorder.

Respiratory Therapy (RT): The therapeutic application of a supply of air to an entrance to the airways at an elevated flow rate with respect to typical respiratory flow rate (flow therapy) and/or at a treatment pressure that is typically positive with respect to atmosphere (pressure therapy).

Ventilator: A mechanical device that provides pressure support to a patient to perform some or all of the work of breathing.

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology. Various versions of such arrangements may be considered in relation to the itemized examples in the following numbered paragraphs.

5.10 Examples of the Present Technology

Example 1. A method of conducting wireless communications with a respiratory therapy device, the method comprising:

establishing, by a control device, an insecure wireless communication channel with the respiratory therapy device;

obtaining, by the control device, a first shared secret via a different channel than the insecure wireless communication channel, the first shared secret being known to the respiratory therapy device;

computing, by the control device, a second shared secret using the first shared secret and data communicated over the insecure wireless communication channel, the second shared secret being known to the respiratory therapy device and being stronger than the first shared secret; and conducting, by the control device, wireless communications with the respiratory therapy device based on the second shared secret.

Example 2. The method of Example 1, wherein computing the second shared secret comprises a Diffie-Hellman key exchange.

Example 3. The method of Example 1, further comprising computing, by the control device, a session key using the second shared secret.

Example 4. The method of Example 3, further comprising using, by the control device, the session key to encrypt and decrypt data communicated with the respiratory therapy device over the wireless channel.

Example 5. The method of Example 1, wherein establishing an insecure wireless communication channel comprises computing, by the control device, a symmetric key known to the respiratory therapy device.

Example 6. The method of Example 1 wherein obtaining the first shared secret via the different channel relies on a physical access of the control device to the respiratory therapy device.

Example 7. The method of Example 6, wherein obtaining the first shared secret comprises scanning, by the control device, a machine-readable form of the first shared secret printed on a housing of the respiratory therapy device.

Example 8. The method of Example 7, wherein the machine-readable form is a barcode.

Example 9. The method of Example 8, wherein the barcode is a QR code.

Example 10. The method of Example 6, wherein obtaining the first shared secret comprises receiving, by the control device, the first shared secret entered via a user interface of the control device.

Example 11. The method of Example 1, further comprising confirming, by the control device, that the second shared secret is known to the respiratory therapy device.

Example 12. The method of Example 11, wherein the confirming comprises:

computing a first hash value using the second shared secret;

receiving from the respiratory therapy device over the insecure wireless communication channel, a second hash value; and comparing the first hash value with the second hash value.

Example 13. The method of Example 12, further comprising, upon the first hash value not being equal to the second hash value, generating user output via a user interface of the control device.

Example 14. The method of any one of Examples 1 to 13, wherein the second shared secret establishes a secure wireless communication channel between the control device and the respiratory therapy device.

Example 15. The method of Example 14, further comprising computing a session key from the second shared secret.

Example 16. The method of Example 14 further comprising sending, by the control device over said secure wireless communication channel, a control parameter for controlling a respiratory therapy operation of the respiratory therapy device.

Example 17. The method of Example 16 wherein the control parameter comprises one of a pressure setting and a flow rate setting.

Example 18. The method of any one of Examples 14 to 17 further comprising receiving, by the control device over said secure wireless communication channel, data relating to respiratory therapy operation of the respiratory therapy device.

Example 19. The method of Example 18 wherein the data comprises any one or more of a number of respiratory events and a time of usage of the respiratory therapy device.

Example 20. A computer-readable data storage medium having program instructions encoded thereon configured to cause a processor to perform a method comprising the method of any one of Examples 1 to 19.

Example 21. A server having access to the computer-readable data storage medium of Example 20, wherein the server is configured to receive requests for downloading the program instructions of the computer-readable data storage medium to the control device over a network.

Example 22. A control device configured to communicate wirelessly with a respiratory therapy device, the control device comprising:

a memory storing processing instructions; and a processor configured to:

establish an insecure wireless communication channel with the respiratory therapy device;

obtain a first shared secret via a different channel than the insecure wireless communication channel, the first shared secret being known to the respiratory therapy device; and compute a second shared secret using the first shared secret and data communicated over the insecure wireless communication channel, the second shared secret being known to the respiratory therapy device and being stronger than the first shared secret.

Example 23. The control device of Example 22, further comprising a barcode reader, wherein the processor is further configured to obtain the first shared secret by utilising the barcode reader to scan a barcode printed on a housing of the respiratory therapy device, the barcode encoding the first shared secret.

Example 24. The control device of Example 22, further comprising a user interface, wherein the processor is further configured to obtain the first shared secret via input entered through the user interface.

Example 25. A method of conducting wireless communications between a respiratory therapy device and a control device, the method comprising:

establishing, by the respiratory therapy device, an insecure wireless communication channel with the control device;

computing, by the respiratory therapy device, a second shared secret using a first shared secret and data communicated over the insecure wireless communication channel, the first shared secret and the second shared secret being known to the control device, the second shared secret being stronger than the first shared secret; and conducting, by the respiratory therapy device, wireless communications with the control device based on the second shared secret.

Example 26. A respiratory therapy device configured to communicate wirelessly with a control device, the respiratory therapy device comprising:
a memory storing processing instructions; and
a controller configured to:
establish an insecure wireless communication channel with the control device; and
compute a second shared secret using a first shared secret and data communicated over the insecure wireless communication channel, the first shared secret and the second shared secret being known to the control device, the second shared secret being stronger than the first shared secret.

Example 27. The respiratory therapy device of Example 26, further comprising a housing including a printed barcode, the printed barcode encoding the first shared secret.

Example 28. A respiratory therapy system comprising:
a respiratory therapy device; and
a control device configured to communicate wirelessly with the respiratory therapy device;
wherein the control device comprises a processor configured to:
establish an insecure wireless communication channel with the respiratory therapy device;
obtain a first shared secret via a different channel than the insecure wireless communication channel, the first shared secret being known to the respiratory therapy device; and
compute a second shared secret using the first shared secret and data communicated over the insecure wireless communication channel, the second shared secret being known to the respiratory therapy device and being stronger than the first shared secret, and
conduct wireless communications with the respiratory therapy device based on the second shared secret.

Example 29. The respiratory therapy system of Example 28, wherein the respiratory therapy device comprises a housing including a printed barcode, the printed barcode encoding the first shared secret.

Example 30. The respiratory therapy system of Example 29, wherein the control device further comprises a barcode reader, wherein the processor is further configured to obtain the first shared secret with the barcode reader by scanning the barcode.

Example 31. The respiratory therapy system of Example 29, wherein the control device further comprises a user interface, wherein the processor is further configured to obtain the first shared secret via input entered through the user interface.

Example 32. A method of uploading therapy data generated by a respiratory therapy device to a remote server via a control device configured to communicate with the respiratory therapy device and to communicate with the remote server, the method comprising:
receiving, by the control device, the therapy data from the respiratory therapy device;
receiving, by the control device, a nonce from the remote server;
sending, by the control device, the nonce to the respiratory therapy device;
receiving, by the control device, a signing key from the respiratory therapy device, wherein the signing key is dependent on the nonce and a secret known to the respiratory therapy device and the remote server;
generating, by the control device, an authorisation code using the therapy data and the signing key, the authorisation code for authenticating the therapy data; and
sending, by the control device, the therapy data and the authorisation code to the remote server.

Example 33. The method of Example 32, wherein the authorisation code is a hashed message authorisation code.

Example 34. The method of any one of Examples 32 to 33, wherein the signing key is further dependent on an offset into the shared secret, the offset being received from the remote server by the control device.

Example 35. The method of any one of Examples 32 to 34, wherein the nonce is a pseudo-random number.

Example 36. The method of any one of Examples 32 to 35, wherein the control device receives the signing key securely from the respiratory therapy device by decrypting the signing key using a symmetric key that is known to the respiratory therapy device.

Example 37. A control device comprising:
a memory, and
a processor,
wherein the memory contains program instructions that when, executed by the processor, control the control device to upload therapy data generated by a respiratory therapy device to a remote server, wherein the program instructions control the control device to:
receive the therapy data from the respiratory therapy device;
receive a nonce from the remote server;
send the nonce to the respiratory therapy device;
receive a signing key from the respiratory therapy device, wherein the signing key is dependent on the nonce and a secret known to the respiratory therapy device and the remote server;
generate an authorisation code using the therapy data and the signing key, the authorisation code for authenticating the therapy data; and
send the therapy data and the authorisation code to the remote server.

Example 38. A method of authenticating therapy data generated by a respiratory therapy device, the method comprising:
receiving the therapy data and a first authorisation code;
computing a signing key from a nonce and a secret that is known to the respiratory therapy device;
computing a second authorisation code from the received therapy data and the signing key; and
authenticating the therapy data by comparing the first authorisation code with the second authorisation code.

Example 39. The method of Example 38, further comprising sending an offset to the respiratory therapy device, wherein the signing key is dependent on the offset.

Example 40. The method of any one of Examples 38 to 39, wherein the authorisation code is a hashed message authorisation code.

Example 41. The method of any one of Examples 38 to 40, further comprising sending the nonce to the respiratory therapy device.

Example 42. The method of any one of Examples 38 to 41, wherein the nonce is a pseudo-random number.

Example 43. A server comprising:
a memory, and
a processor,
wherein the memory contains program instructions that, when executed by the processor, control the server to authenticate therapy data generated by a respiratory therapy device, wherein the program instructions control the server to:
receive the therapy data and a first authorisation code;
compute a signing key from a nonce and a secret that is known to the respiratory therapy device;
compute a second authorisation code from the received therapy data and the signing key; and
authenticate the therapy data by comparing the first authorisation code with the second authorisation code.

Example 44. A networked respiratory therapy system comprising:
a respiratory therapy device configured to deliver respiratory therapy to a patient;
a remote server; and
a control device configured to communicate with the respiratory therapy device and to communicate with the remote server, the control device being configured to:
receive, by the control device, therapy data from the respiratory therapy device;
receive, by the control device, a nonce from the remote server;
send, by the control device, the nonce to the respiratory therapy device;
receive, by the control device, a signing key from the respiratory therapy device, wherein the signing key is dependent on the nonce and a secret known to the respiratory therapy device and the remote server;
generate, by the control device, an authorisation code using the therapy data and the signing key, the authorisation code for authenticating the therapy data; and
send, by the control device, the therapy data and the authorisation code to the remote server.

Example 45. The system of Example 44, wherein the respiratory therapy device is a respiratory pressure therapy device.

Example 46. The system of any one of Examples 44 to 45, wherein the control device is configured to communicate securely with the respiratory therapy device using a shared symmetric key.

Example 47. The system of any one of Examples 44 to 46, wherein the remote server is configured to:
receive the therapy data and a first authorisation code;
compute a signing key from a nonce and a secret that is known to the respiratory therapy device;
compute a second authorisation code from the received therapy data and the signing key; and
authenticate the therapy data by comparing the first authorisation code with the second authorisation code.

Example 48. A networked respiratory therapy system comprising:
a respiratory therapy device configured to deliver respiratory therapy to a patient;
a control device configured to communicate with the respiratory therapy device; and
a remote server configured to communicate with the control device, the remote server being configured to:
receive therapy data and a first authorisation code from the control device;
compute a signing key from a nonce and a secret that is known to the respiratory therapy device;
compute a second authorisation code from the received therapy data and the signing key; and
authenticate the therapy data by comparing the first authorisation code with the second authorisation code.

Example 49. The system of Example 48, wherein the respiratory therapy device is a respiratory pressure therapy device.

Example 50. The system of any one of Examples 48 to 49, wherein the control device is configured to communicate securely with the respiratory therapy device using a shared symmetric key.

Example 51. The system of any one of Examples 48 to 50, wherein the control device is configured to:
receive the therapy data from the respiratory therapy device;
receive a nonce from the remote server;
send the nonce to the respiratory therapy device;
receive a signing key from the respiratory therapy device, wherein the signing key is dependent on the nonce and a secret known to the respiratory therapy device and the remote server;
generate an authorisation code using the therapy data and the signing key, the authorisation code for authenticating the therapy data; and
send the therapy data and the authorisation code to the remote server.

Example 52. The system of any one of Examples 48 to 50, wherein the respiratory therapy device is configured to:
receive a nonce from the remote server;
compute a signing key from the nonce and a secret known to the respiratory therapy device and the remote server;
generate an authorisation code using the therapy data and the signing key; and
send the therapy data and the authorisation code to the remote server.

Example 53. A method of uploading therapy data generated by a respiratory therapy device to a remote server, the method comprising:
receiving, by the respiratory therapy device, a nonce from the remote server;
computing, by the respiratory therapy device, a signing key from the nonce and a secret known to the remote server;
generating, by the respiratory therapy device, an authorisation code using the therapy data and the signing key, the authorisation code for authenticating the therapy data; and
sending, by the respiratory therapy device, the therapy data and the authorisation code to the remote server.

Example 54. The method of Example 53, wherein the authorisation code is a hashed message authorisation code.

Example 55. The method of any one of Examples 53 to 54, wherein the signing key is further dependent on an offset into the shared secret, the offset being received from the remote server by the respiratory therapy device.

Example 56. The method of any one of Examples 53 to 55, wherein the nonce is a pseudo-random number.

Example 57. The method of any one of Examples 53 to 56, wherein the respiratory therapy device receives the nonce via a control device configured to communicate with the remote server.

Example 58. The method of Example 57, wherein the respiratory therapy device receives the nonce from the control device by decrypting the nonce using a symmetric key that is known to the control device.

Example 59. The method of any one of Examples 53 to 58, wherein the respiratory therapy device sends the therapy data and the authorisation code via a control device configured to communicate with the remote server.

Example 60. The method of Example 59, wherein the control device sends the therapy data and the authorisation code to the control device by encrypting the therapy data and the authorisation code using a symmetric key that is known to the control device.

Example 61. A respiratory therapy device comprising:
a pressure generator adapted to couple with a patient interface and to supply a flow of air at positive pressure to the patient interface;
a memory, and
a processor,
wherein the memory contains program instructions that, when executed by the processor, control the respiratory therapy device to upload therapy data generated by the respiratory therapy device to a remote server, wherein the program instructions control the respiratory therapy device to:
receive a nonce from the remote server;
compute a signing key from the nonce and a secret known to the remote server;
generate an authorisation code using the therapy data and the signing key, the authorisation code for authenticating the therapy data; and
send the therapy data and the authorisation code to the remote server.

Example 62. A networked respiratory therapy system comprising:
a respiratory therapy device for delivery of respiratory therapy to a patient; and
a remote server configured to communicate with the respiratory therapy device;
wherein the respiratory therapy device is configured to:
receive a nonce from the remote server;
compute a signing key from the nonce and a secret known to the remote server;
generate an authorisation code using therapy data and the signing key, the authorisation code for authenticating the therapy data; and
send the therapy data and the authorisation code to the remote server.

Example 63. The system of Example 62, wherein the respiratory therapy device is a respiratory pressure therapy device.

Example 64. The system of any one of Examples 62 to 63, further comprising a control device configured to communicate securely with the respiratory therapy device and to communicate with the remote server.

Example 65. The system of Example 64, wherein the control device is configured to communicate securely with the respiratory therapy device using a symmetric key that is known to the respiratory therapy device.

Example 66. The system of any one of Examples 62 to 65, wherein the remote server is configured to:
receive the therapy data and a first authorisation code;
compute a signing key from a nonce and a secret that is known to the respiratory therapy device;
compute a second authorisation code from the received therapy data and the signing key; and
authenticate the therapy data by comparing the first authorisation code with the second authorisation code.

Example 67. Apparatus comprising:
means for receiving therapy data from a respiratory therapy device;
means for receiving a nonce from a remote server;
means for sending the nonce to the respiratory therapy device;
means for receiving a signing key from the respiratory therapy device, wherein the signing key is dependent on the nonce and a secret known to the respiratory therapy device and the remote server;
means for generating an authorisation code using the therapy data and the signing key, the authorisation code for authenticating the therapy data; and
means for sending the therapy data and the authorisation code to the remote server.

Example 68. Apparatus comprising:
means for receiving therapy data from a respiratory therapy device and a first authorisation code;
means for computing a signing key from a nonce and a secret that is known to the respiratory therapy device;
means for computing a second authorisation code from the received therapy data and the signing key; and
means for authenticating the therapy data by comparing the first authorisation code with the second authorisation code.

Example 69. Apparatus comprising:
means for delivering respiratory therapy to a patient;
means for receiving a nonce from a remote server;
means for computing a signing key from the nonce and a secret known to the remote server;
means for generating an authorisation code using therapy data and the signing key, the authorisation code for authenticating the therapy data; and
means for sending the therapy data and the authorisation code to the remote server.

5.11 Reference Signs List patient 1000
bed partner 1100
patient interface 3000
seal-forming structure 3100
plenum chamber 3200
structure 3300
vent 3400
connection port 3600
forehead support 3700
RT device 4000
external housing 4010
upper portion 4012
portion 4014
panel 4015
chassis 4016
handle 4018
pneumatic block 4020
air filter 4110
inlet air filter 4112
outlet air filter 4114
mufflers 4120
inlet muffler 4122
outlet muffler 4124
pressure generator 4140
blower 4142
motor 4144
anti-spill back valve 4160
air circuit 4170
electrical components 4200
PCBA 4202
electrical power supply 4210
button 4220
central controller 4230 clock 4232
therapy device controller 4240
protection circuits 4250
memory 4260
transducers 4270
pressure sensors 4272
flow rate sensor 4274
motor speed transducer 4276
interface 4280
remote external communication network 4282
local external communication network 4284
remote external device 4286
local external device 4288
output device 4290
humidifier 5000
humidifier inlet 5002
humidifier outlet 5004
humidifier base 5006
humidifier reservoir 5110
humidifier reservoir dock 5130
heating element 5240
networked respiratory therapy system 6000
control device 6010
channel 6013
wireless connection 6015
barcode 6017
second control device 6020
wireless connection 6025
malefactor 6030
server 6040
wireless connection 6050
unassociated control device 6060
malefactor 6065
wireless connection 6070
method 7000
step 7010
step 7020
step 7030
method 8000
arrow 8001
step 8010
step 8015
step 8020
step 8025
step 8030
step 8035
step 8040
step 8045
method 8050
step 8055
step 8060
step 8065
step 8070
step 8075
step 8080
step 8085
step 8090
step 8095
method 9000
step 9005
step 9010
step 9020
step 9030
step 9035
step 9040
step 9045
step 9050
step 9055
step 9060
step 9065
method 10000
step 10005
step 10010
step 10015
step 10020
step 10025
step 10030
step 10035
step 10040
step 10045
method 11000
step 11005
step 11010
step 11015
step 11020
step 11025
step 11030
step 11040
step 10045

6 CITATIONS

1. Simple Pairing Whitepaper, version 10r00. Bluetooth Core Specification Working Group, August 2006.
2. Using the Secure Remote Password (SRP) Protocol for TLS Authentication (RFC-5054), Taylor et al., November 2007.

The invention claimed is:

1. A method of uploading therapy data generated by a respiratory therapy device to a remote server via a control device configured to communicate with the respiratory therapy device and to communicate with the remote server, the method comprising:
   receiving, by the control device, the therapy data from the respiratory therapy device;
   receiving, by the control device, a nonce from the remote server;
   sending, by the control device, the nonce to the respiratory therapy device;
   receiving, by the control device, a signing key from the respiratory therapy device, wherein the signing key is dependent on the nonce and a secret known to the respiratory therapy device and the remote server;
   generating, by the control device, an authorisation code using the therapy data and the signing key, the authorisation code for authenticating the therapy data; and
   sending, by the control device, the therapy data and the authorisation code to the remote server.

2. The method of claim 1, wherein the authorisation code is a hashed message authorisation code.

3. The method of claim 1, wherein the signing key is further dependent on an offset into the shared secret, the offset being received from the remote server by the control device.

4. The method of claim 1, wherein the nonce is a pseudo-random number.

5. The method of claim 1, wherein the control device receives the signing key securely from the respiratory therapy device by decrypting the signing key using a symmetric key that is known to the respiratory therapy device.

6. A control device comprising:
   a memory, and
   a processor, wherein the memory contains program instructions that when, executed by the processor, control the control device to upload therapy data generated by a respiratory therapy device to a remote server, wherein the program instructions control the control device to:
   receive the therapy data from the respiratory therapy device;
   receive a nonce from the remote server;
   send the nonce to the respiratory therapy device;
   receive a signing key from the respiratory therapy device, wherein the signing key is dependent on the nonce and a secret known to the respiratory therapy device and the remote server;
   generate an authorisation code using the therapy data and the signing key, the authorisation code for authenticating the therapy data; and
   send the therapy data and the authorisation code to the remote server.

7. A method of authenticating therapy data generated by a respiratory therapy device, the method comprising:
   receiving the therapy data and a first authorisation code;
   computing a signing key from a nonce and a secret that is known to the respiratory therapy device;
   computing a second authorisation code from the received therapy data and the signing key; and
   authenticating the therapy data by comparing the first authorisation code with the second authorisation code.

8. The method of claim 7, further comprising sending an offset to the respiratory therapy device, wherein the signing key is dependent on the offset.

9. The method of claim 7, wherein the authorisation code is a hashed message authorisation code.

10. The method of claim 7, further comprising sending the nonce to the respiratory therapy device.

11. The method of claim 7, wherein the nonce is a pseudo-random number.

12. A server comprising:
   a memory, and
   a processor,
   wherein the memory contains program instructions that, when executed by the processor, control the server to authenticate therapy data generated by a respiratory therapy device, wherein the program instructions control the server to:
      receive the therapy data and a first authorisation code;
      compute a signing key from a nonce and a secret that is known to the respiratory therapy device;
      compute a second authorisation code from the received therapy data and the signing key; and
      authenticate the therapy data by comparing the first authorisation code with the second authorisation code.

13. A method of uploading therapy data generated by a respiratory therapy device to a remote server, the method comprising:
   receiving, by the respiratory therapy device, a nonce from the remote server;
   computing, by the respiratory therapy device, a signing key from the nonce and a secret known to the remote server;
   generating, by the respiratory therapy device, an authorisation code using the therapy data and the signing key, the authorisation code for authenticating the therapy data; and
   sending, by the respiratory therapy device, the therapy data and the authorisation code to the remote server.

14. The method of claim 13, wherein the authorisation code is a hashed message authorisation code.

15. The method of claim 13, wherein the signing key is further dependent on an offset into the shared secret, the offset being received from the remote server by the respiratory therapy device.

16. The method of claim 13, wherein the nonce is a pseudo-random number.

17. The method of claim 13, wherein the respiratory therapy device receives the nonce via a control device configured to communicate with the remote server.

18. The method of claim 17, wherein the respiratory therapy device receives the nonce from the control device by decrypting the nonce using a symmetric key that is known to the control device.

19. The method of claim 13, wherein the respiratory therapy device sends the therapy data and the authorisation code via a control device configured to communicate with the remote server.

20. The method of claim 19, wherein the control device sends the therapy data and the authorisation code to the control device by encrypting the therapy data and the authorisation code using a symmetric key that is known to the control device.

21. A respiratory therapy device comprising:
   a pressure generator adapted to couple with a patient interface and to supply a flow of air at positive pressure to the patient interface;
   a memory, and
   a processor,
   wherein the memory contains program instructions that, when executed by the processor, control the respiratory therapy device to upload therapy data generated by the respiratory therapy device to a remote server, wherein the program instructions control the respiratory therapy device to:
      receive a nonce from the remote server;
      compute a signing key from the nonce and a secret known to the remote server;
      generate an authorisation code using the therapy data and the signing key, the authorisation code for authenticating the therapy data; and
      send the therapy data and the authorisation code to the remote server.

* * * * *